(12) United States Patent
Soderman

(10) Patent No.: US 7,221,783 B2
(45) Date of Patent: May 22, 2007

(54) METHOD AND ARRANGEMENT FOR REDUCING NOISE

(75) Inventor: Tobias Soderman, Balinge (SE)

(73) Assignee: Gyros Patent AB, Uppsala (SE)

( * ) Notice: Subject to any disclaimer, the term of this patent is extended or adjusted under 35 U.S.C. 154(b) by 756 days.

(21) Appl. No.: 10/331,399

(22) Filed: Dec. 30, 2002

(65) Prior Publication Data

US 2003/0156763 A1 Aug. 21, 2003

Related U.S. Application Data

(63) Continuation-in-part of application No. 10/062,258, filed on Jan. 31, 2002.

(30) Foreign Application Priority Data

Dec. 31, 2001 (SE) .................................. 0104461
Sep. 17, 2002 (WO) ..................... PCT/SE02/01678

(51) Int. Cl.
*G06K 9/00* (2006.01)

(52) U.S. Cl. ....................... 382/128; 382/275

(58) Field of Classification Search ................ 382/130, 382/275, 128, 278
See application file for complete search history.

(56) References Cited

U.S. PATENT DOCUMENTS

| 5,376,252 | A | | 12/1994 | Ekstrom | |
|---|---|---|---|---|---|
| 5,633,509 | A | * | 5/1997 | Takeo | ........................ 250/584 |
| 5,690,841 | A | | 11/1997 | Elderstig | |
| 5,773,488 | A | | 6/1998 | Allmer | |
| 5,805,742 | A | * | 9/1998 | Whitsitt | ...................... 382/275 |
| 5,892,539 | A | | 4/1999 | Colvin | |
| 5,892,577 | A | | 4/1999 | Gordon | |
| 5,962,081 | A | | 10/1999 | Ohman | |
| 5,994,150 | A | | 11/1999 | Challener et al. | |
| 5,995,209 | A | | 11/1999 | Ohman | |
| 6,126,765 | A | | 10/2000 | Ohman | |
| 6,144,447 | A | | 11/2000 | Ohman | |
| 6,192,768 | B1 | | 2/2001 | Wallman | |

(Continued)

FOREIGN PATENT DOCUMENTS

EP 0 392 475 A2 10/1990

(Continued)

OTHER PUBLICATIONS

Duffy, David C., et al.; Microfabricated Centrifugal Microfluidic Systems: Characterization and Multiple Enzymatic Assays; anal. Chem. 71: 4669-4678-1999.

(Continued)

*Primary Examiner*—Matthew C. Bella
*Assistant Examiner*—Dennis Rosario
(74) *Attorney, Agent, or Firm*—Fulbright & Jaworski LLP

(57) ABSTRACT

The present invention concerns a method and an arrangement for reducing noise in a substance raw data image containing noise. The method may comprise following steps in any order for removing different noise signals contributions step-by-step in any order in a substance raw data image: reducing background radiation; reducing peak disturbance; locating the detection area within the search area; moving binary artifacts; removing unwanted areas of the detection area; and applying default detection area in noisy images). The present invention also relates to a method and an arrangement for determining a measure of at least one substance.

9 Claims, 12 Drawing Sheets

U.S. PATENT DOCUMENTS

| | | |
|---|---|---|
| 6,203,291 B1 | 3/2001 | Stemme |
| 6,322,682 B1 | 11/2001 | Arvidsson |
| 6,338,820 B1 | 1/2002 | Hubbard et al. |
| 6,339,473 B1 | 1/2002 | Gordon |
| 6,454,970 B1 | 9/2002 | Ohman |
| 6,620,478 B1 | 9/2003 | Ohman |
| 6,632,656 B1 | 10/2003 | Thomas |
| 6,653,625 B2 | 11/2003 | Andersson |
| 6,707,488 B1 * | 3/2004 | Anuashvili et al. ......... 348/169 |
| 6,717,136 B2 | 4/2004 | Andersson |
| 6,728,644 B2 | 4/2004 | Bielik |
| 6,811,736 B1 | 11/2004 | Ohman |
| 6,812,456 B2 | 11/2004 | Andersson |
| 6,812,457 B2 | 11/2004 | Andersson |
| 2003/0044322 A1 | 3/2003 | Andersson |
| 2003/0047823 A1 | 3/2003 | Ohman |
| 2003/0053934 A1 | 3/2003 | Andersson |
| 2003/0054563 A1 | 3/2003 | Ljungstrom |
| 2003/0082075 A1 | 5/2003 | Agren |
| 2003/0094502 A1 | 5/2003 | Andersson |
| 2003/0129360 A1 | 7/2003 | Derand |
| 2003/0211012 A1 | 11/2003 | Bergstrom |
| 2003/0213551 A1 | 11/2003 | Derand |
| 2003/0231312 A1 | 12/2003 | Sjoberg |
| 2004/0058408 A1 | 3/2004 | Thomas |
| 2004/0096867 A1 | 5/2004 | Andersson |
| 2004/0099310 A1 | 5/2004 | Andersson |
| 2004/0120856 A1 | 6/2004 | Andersson |
| 2004/0202579 A1 | 10/2004 | Larsson et al. |

FOREIGN PATENT DOCUMENTS

| | | |
|---|---|---|
| EP | 0 534 601 A2 | 3/1993 |
| EP | 0601714 B1 | 3/2000 |
| WO | WO-96/09548 A1 | 3/1996 |
| WO | WO-97/21090 A1 | 6/1997 |
| WO | WO-99/09394 A1 | 2/1999 |
| WO | WO 2000/07026 | 2/2000 |
| WO | WO-00/40750 A1 | 7/2000 |
| WO | WO-00/40957 A1 | 7/2000 |
| WO | WO-00/67635 A1 | 11/2000 |
| WO | WO 200148459 A1 * | 7/2001 |
| WO | WO-02/14838 A2 | 2/2002 |
| WO | WO-03/025548 A1 | 3/2003 |

OTHER PUBLICATIONS

U.S. Appl. No. 09/937,533, Larsson et al.
U.S. Appl. No. 10/169,056, Andersson et al.
U.S. Appl. No. 10/276,282, Larsson et al.
U.S. Appl. No. 10/402,138, Kylberg et al.
U.S. Appl. No. 09/958,577, Ulfendahl.
U.S. Appl. No. 09/869,554, Orlefors et al.
U.S. Appl. No. 09/830,475, Stjernstrom.
U.S. Appl. No. 10/168,942, Tooke et al.
U.S. Appl. No. 10/957,452, Ekstrand et al.
U.S. Appl. No. 10/070,912, Ohman et al.
U.S. Appl. No. 10/402,137, Kylberg et al.
U.S. Appl. No. 10/030,297, Derand et al.
U.S. Appl. No. 10/924,151, Tooke et al.
U.S. Appl. No. 10/513,084, Holmquest et al.
U.S. Appl. No. 09/937,533, Derand et al.
U.S. Appl. No. 10/999,532, Ostlin et al.
U.S. Appl. No. 10/867,893, Derand et al.
U.S. Appl. No. 11/017,252, Derand et al.
U.S. Appl. No. 10/182,792, Derand et al.
U.S. Appl. No. 10/450,177, Ohman et al.
U.S. Appl. No. 10/129,032, Tormod.
U.S. Appl. No. 09/674,457, Larsson et al.
U.S. Appl. No. 10/069,827, Derand et al.
U.S. Appl. No. 10/244,667, Agren.
U.S. Appl. No. 10/849,321, Flelden et al.
U.S. Appl. No. 10/111,822, Tooke et al.
Office Action issued by the European Patent Office for EP 02 793 749.9, dated Nov. 15, 2006.

* cited by examiner

METHOD AND ARRANGEMENT FOR REDUCING NOISE

This application is a continuation-in-part of U.S. application Ser. No. 10/062,258 filed on Jan. 31, 2002 and priority to Swedish Application No. SE0104464-9 filed on Dec. 31, 2001, and International Application No. PCT/SE02/01678 filed on Sep. 17, 2002.

BACKGROUND OF THE INVENTION

I. Field of Invention

The present invention generally concerns the field of microfluidic devices. More particularly, the present invention concerns a method and an arrangement for reducing noise in a substance raw data image containing noise. The present invention also relates to a method and an arrangement for determining a measure of at least one substance. The substance raw data image has been obtained from a search area that comprises a detection area associated with a detection microcavity that is part of a microchannel structure of a microfluidic device detectable signals.

The substance raw data image reflects from a substance that is present in the detection microcavity after one or more liquid aliquots have been processed through the microchannel structure that comprises the detection microcavity.

II. Related Art

All patents and patent applications cited in this specification are incorporated by reference in their entirety.

A. Background Publications

Detector arrangements for measuring radiation signals from individual detection areas on a circular substrate have been described in a number of previous publications. See for instance: EP 392475 (Idemitsu Petrochemical Co, Yamaji Kazutaka et al.) U.S. Pat. No. 5,994,150 (Imation Corp, Challener et al.), U.S. Pat. No. 5,892,577 (The University Court of the University of Glasgow, Gordon), WO 9721090 (Gamera, Mian et al.), Duffy et al., "Microfabricated Centrifugal Microfluidic systems: Characterization and multiple Enzymatic Assays" (Anal. Chem. 71 (1999) 4669–4678), WO 0040857 (Amersham Pharmacia Biotech AB, Björkesten et al.)

B. Background Technology and Problems

The present invention belongs to the field of miniaturization of processes which comprise sample treatment, assay protocols, chemical and/or biochemical synthesis etc., within medicine, chemistry, biochemistry, molecular biology and the like. At present one important goal within this field is to reduce the costs for these processes, for instance to reduce the amount of reagents needed per assay, reduce time per assay, etc. One route has been to increase the degree of parallelity, for instance by integrating as many as possible of similar process runs in one and the same device in order to carry out all the runs in parallel. At present, large numbers of research groups and companies are involved in developing technology that will solve the numerous problems encountered.

One problem is related to the optimal way of configuring the detector in relation to the microdevice used for performing the processes while maintaining an acceptable sensitivity and reproducibility. This problem may become particularly pronounced if the measuring step is performed by continuously moving the detector unit and the detection areas of a microfluidic device relative to each other during the measurement operation.

Another problem arises if the microfluidic device is in the form of a disc which is skewed because then it becomes difficult to maintain the optical focus in the right position relative to the detection areas. Without proper arrangement skewed discs will reduce sensitivity. This problem in particular applies to discs made of plastic material.

Another problem is related to maintaining an acceptable sensitivity and reproducibility when changing sample volumes from the µl-range to the nl-range and performing the process protocols with a high degree of parallelity within the same device. The inventors have found that under these circumstances the materials from which the microfluidic devices are fabricated and the various treatments during the manufacturing and conditioning of the devices easily introduce signal artifacts that are of the same kind and of comparable or larger size as the desired signals.

During recent years it has become popular to fabricate microfluidic devices in plastic material. This kind of material is typically highly fluorescent ("auto-fluorescent") with emission wavelengths covering most of the wavelengths normally utilized in fluorescent measurements. Compared to microtitre wells and other uncovered microstructures the problem becomes more severe for the kind of covered microchannel structures used in the present invention, because the exciting and emitted radiation has to pass through plastic material. For transparent plastic material there is also a problem with "cross-talks" between the detection area/detection microcavities. Similar problems may also be at hand for spectroscopic methods in which the radiation to be measured is created within the detection microcavity (for instance chemiluminescence, bioluminescence, etc.,).

A more recent problem relates to the fact that the present assignee recently has managed to control the liquid flow in microfluidic devices containing a plurality of microchannel structures in such a way that the inter-channel variation for a device with respect to flow becomes insignificant. This progress has enabled the assignee to quantify with a low inter-assay variation and a high sensitivity analytes, such as antigens, in the subfemtomole range in nl-volumes by carrying out the solid phase reaction of a heterogeneous sandwich immunoassay under flow conditions in small columns (nl-columns). This has raised the question about measuring the amount of an affinity complex such as an immune complex as a function of position along the flow direction in a column. See WO 02075312 (Gyros AB) and assignee's poster presented on Sep. 17, 2001 at Proteomic Forum Sep. 16–19, 2001, Munich, Germany.

BRIEF SUMMARY OF THE INVENTION

The present invention is directed to an arrangement and method for reducing noise in a substance raw data image containing noise. The present invention also is directed to a method and an arrangement for determining a measure of at least one substance. The substance raw data image has been obtained from a search area that comprises a detection area associated with a detection microcavity that is part of a microchannel structure of a microfluidic device detectable signals.

A first object is to reduce the electronic, chemical, optical and dust noise that is present in the stored measurement data of a search area, i.e., that is present in the stored image of a detection area. Electronic noise is introduced by the detector arrangement instrument. The optical noise arises from the design of the disc, the lid of the disc (if present), the detector head (e.g., lenses), etc. The chemical noise arise from chemicals and materials used in the manufacture of the disc and from undesired reactions including undesired adsorption related to the various reagents and solutions that have been used for placing the signal creating substance in the detection microcavity. Peak noise may derive from the manufacturing or the processing of the disc. Different kinds of dust, like particles, fibers, hair, etc may also introduce peak noise. The invention typically reduces noise from steps related to chemical noise, e.g., disturbing fluorescence in the case the substance raw data image is based on fluorescence.

A second object is to provide a method, software and arrangement for treating radiation data from one or more detection areas of the kind of microfluidic device described herein.

A third object is to provide arrangement, software and methods enabling accurate integration of radiation deriving from a desired substance as a function of subareas of individual detection areas. In particular this object aims at avoiding the problems discussed herein which the inventors have found may appear when measuring low amounts of substances with a high accuracy in microfluidic devices.

These objects in particular apply to radiation data that have been collected while the detection area(s) is(are) moved in front of the detector head that is used for collection of the data, or vice versa, e.g., the detection area(s) is/are present in the surface of a circular disc that is spun in front of the detector head.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

It is readily apparent to one skilled in the art that various embodiments and modifications can be made to the invention disclosed in this Application without departing from the scope and spirit of the invention.

As used herein, the use of the word "a" or "an" when used in conjunction with the term "comprising" in the sentences and/or the specification may mean "one," but it is also consistent with the meaning of "one or more," "at least one," and "one or more than one."

As used herein, the term "rotating" refers to spinning. Yet further, the term "rotating" may also include, but is not limited to a step-wise rotation of a disc.

As used herein, the term "reagent" includes, but is not limited to an analyte.

As used herein, the term "in a circular manner" refers to around the center of the disc (circumferential direction).

The term "a plurality of microchannel structures" means two, three or more microchannel structures. Typically the term "plurality" means $\geq 10$, such $\geq 50$ or $\geq 100$ microchannel structures.

The terms "removing noise" and "reducing noise" means that the noise contribution in the measured data (values) is reduced to zero, or is negligible. The words "reduce" and "remove" are used alternately in the text, but there is no difference in the meaning of the two words in this specification. They are regarded as equivalent.

Figure 1:
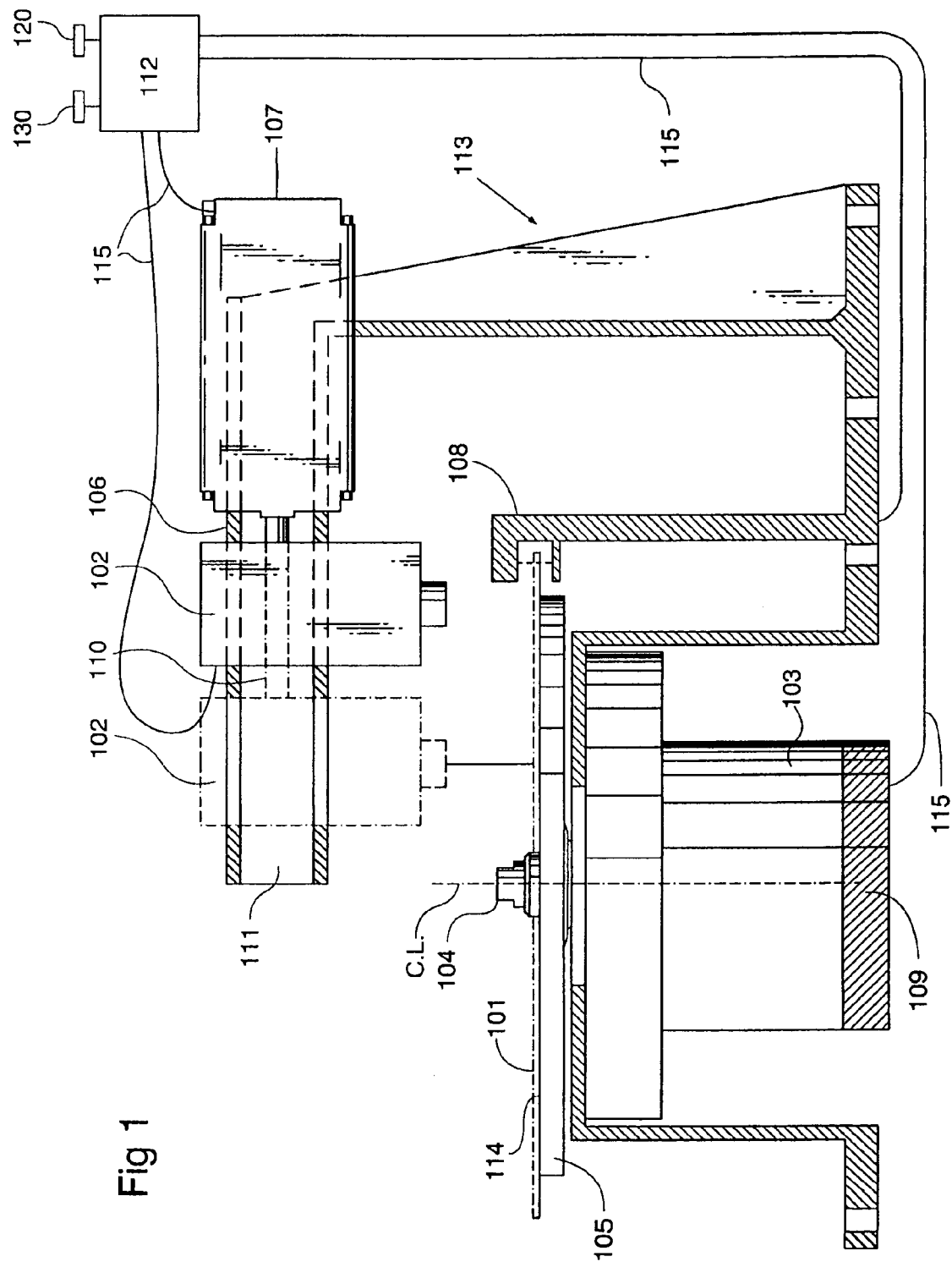
FIG. 1 illustrates a schematic view on an arrangement of the invention and its main parts.
Figure 3:
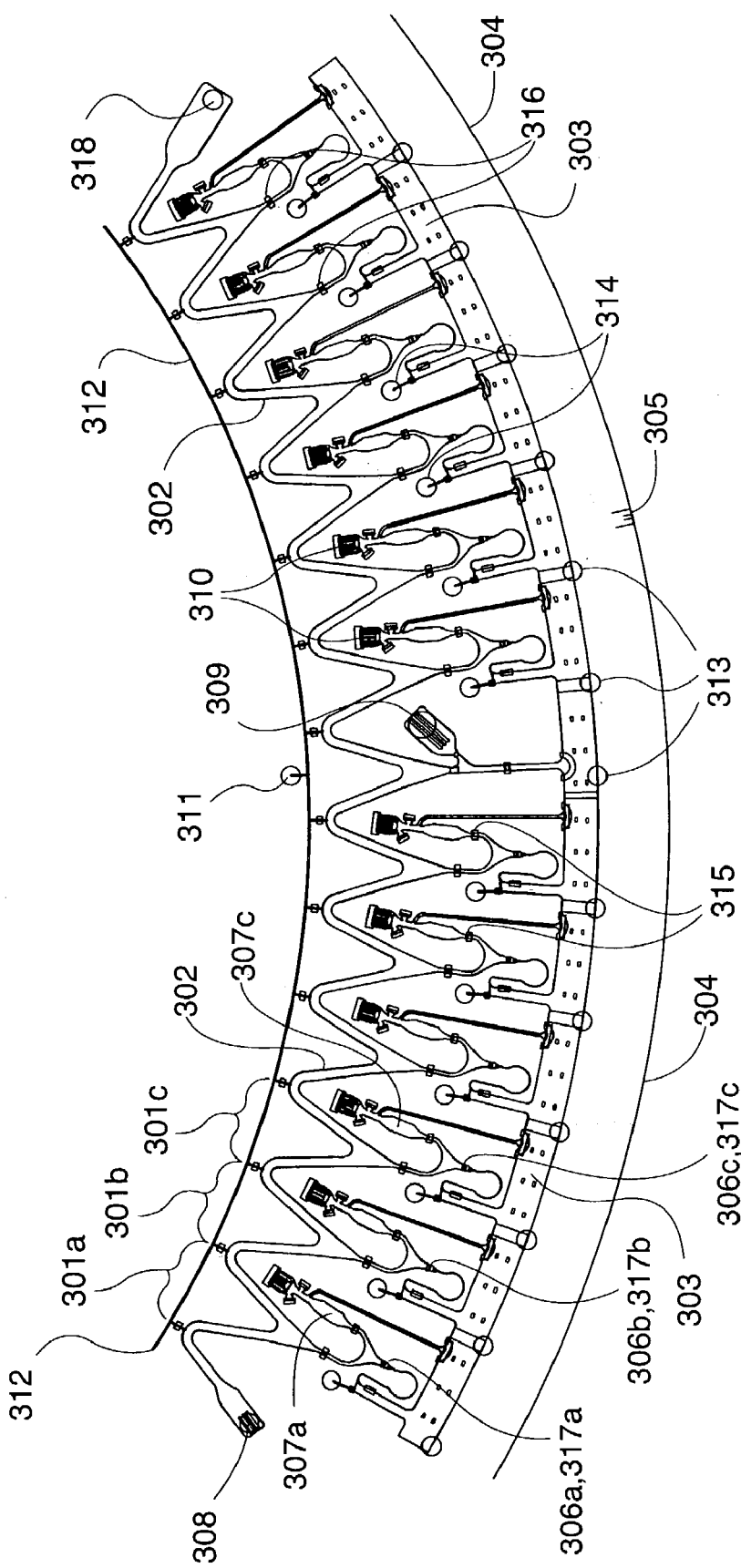
FIG. 3 illustrates a set of microchannel structures that can be used in a circular disc.

As illustrated in FIG. 1, a detector arrangement is typically adapted for measuring radiation from a plurality of detection areas (317$a,b,c$, etc., in FIG. 3) each of which is associated with a detection microcavity (306$a,b,c$, etc., in FIG. 3) in a microfluidic disc (101 in FIG. 1, 301 in FIG. 3). With reference to FIG. 1, the arrangement comprises:

(a) a detector head (102) with a focal area, and a disc holder (105) which are linked to a means enabling for the detector head (102), i.e., the focal area to transverse, the surface of the disc (101) in an essentially circular (means I) and/or radial manner (means II) when the disc is placed in the disc holder (105)

(b) an angular aligning system (108,109) for recognizing the angular position of the part area which at a particular time is covered by the focal area, and (c) an optional radial aligning system (110,111) for recognizing the radial position of the part area which at a particular time is covered by the focal area, and (d) a controller (112), e.g., computer with software, which controls (i) means I and means II causing the focal area to transverse the detection areas (317$a',b',c'$, etc.) in an annular zone of the disc, and (ii) the detector head (102) successively collects radiation in a preselected manner from individual subareas of essentially the same size as the focal area within at least one of the detection areas in said annular zone.

In specific aspects, it is contemplated that the disc holder (105) is linked to at least one of the means for enabling the detector head and the disc to move relative to each other so that the focal area transverses the surface of the disc. Thus, the disc holder (105) is linked to either means I or means II or both means I and means II.

Yet further, it is also understood by those of skill in the art that means I, means II, and the detector head can be linked directly or indirectly to the controller.

Means I comprises three main variants with respect to how the disc and detector moves:
(1) The disc is rotating around its axis of symmetry. In this variant, means I preferably comprises a spinner motor (103) and a shaft (104) carrying the disk holder (105). See FIG. 1.
(2) The detector head (focal area) is circularly moving around the axis of symmetry of the disc. In this variant, means I preferably comprises a spinner motor and a shaft with an arm that carries the detector head. This shaft typically has the same direction as the axis of symmetry of the disc when placed on the disc holder.
(3) A combination of (1) and (2).

Means II comprises three main variants with respect to how the disc and detector head moves:
(1) The disc is laterally moving in front of the detector head. In this variant, means II preferably comprises a motor for laterally moving the disc holder.
(2) The detector head (focal area) is laterally moving over the disc surface. In this variant, means II preferably comprises a linear frame (106) that carries the detector head, and a drive unit (107) for radial movement of the focal area, over a disc which is placed in the disc holder (105). See FIG. 1.
(3) A combination of (1) and (2).

The arrangement is illustrated in FIG. 1.

I. Means I and the Angular Aligning System for the Detector Head

In a typical variant, the detector head (102) and the motor (103) (e.g., a spinner) with a rotatable shaft (104) carrying a disc holder (105) are supported on a frame structure (113). The motor (103) controls the rotating speed that can be varied, e.g., within an interval between 0–15,000 rpm, such as within an interval between 60–5,000 rpm. The rotation of the disc may be stepwise. When the disc is rotating, the focal area of the detector head will successively scan angularly adjacent part areas of the disc surface. Means I in FIG. 1 is according to variant (1) above and comprises the motor (103) and the shaft (104).

The disc holder (105) is preferably a plate on which the disc can be placed. The disc holder could also be a device that holds the disc at its periphery. In order to reduce wobbling of the disc (if the disc is skewed), the side (114) of the plate facing the disc may comprise a system of evenly distributed uncovered shallow grooves or channel openings that are connected to a vacuum system by which the disc can be sucked to the plate. See for instance PCT/SE02/01682 (Gyros AB).

Detection areas may be present in one or both sides of the disc. If the disc holder is in the form of a plate as illustrated in FIG. 1 and the microfluidic disc has detection areas on the side opposing, it is important to secure the plate so as not to disturb the collection of radiation. The plate may thus have a smaller diameter than the disc with the detector areas being located in an annular zone that is not covered by the plate. Alternatively, the plate may be in a material that is translucent for the radiation utilized for the measurement, at least at the detector areas.

The angular aligning system may comprise:
(1) a device that will enable the determination of when a predetermined angular position of a disc placed on the disc holder is in front of the objective of the detector head (102) (i.e., covered by the focal area), and/or
(2) a home position mark detector (108) which is able to detect when a home position mark (305) on a rotating disc (101) placed on the disc holder (105) is passing.

A home position mark (305 in FIG. 3) is preferably placed in an outer circumferential zone outside the detection areas or in some other position, which can be detected with high accuracy. The position coordinates of each specific spot of the surface of the disc is given as the angular position relative to the home position mark and as the radial position relative to the circumference or axis of symmetry or relative to any other arbitrary fixed position on the disc.

A home position mark detector (108) typically has a fixed position outside the disc, for instance on the frame structure (113).

An accurate and preferred alternative for determining when a predetermined angular position is in front of the objective is to include an encoder that progressively gives the angular distance from the home position mark while the disc is rotating. This kind of encoder (109) is typically associated with means I, for instance the motor (103), the shaft (104) or the disc holder (105). By associating the encoder directly with the disc (101) it is likely that the most accurate determination will be accomplished. The encoder typically divides each revolution of the shaft into a large number of grades, for instance >5 000, such as >10 000 or >20 000 or >30 000. A simple but less accurate alternative is to include calculating means that calculates the time needed from a preset rotation speed and the angular distance between the predetermined position and the home position mark (i.e., from the preset rotation speed and the angular position co-ordinate). This kind of calculating means may be associated with the controller.

The angular aligning system should be able to give the angular position coordinate for the part of the disc which is in front of the objective with an accuracy of ±1°, such as within ±0.1° or within ±0.01° (provided there are 360° per revolution). The exact accuracy needed will depend on the size of the disc, radial position of the detection area, the required sensitivity, size of detection area, etc.

II. Means II and the Radial Aligning System for the Detector Head

The detector head (102) is guided on a linear frame (106) that may be the upper part of the frame structure (113) for linear displacement and positioning in a first plane P1, transversely through the central axis CL of shaft (104) and running in a radial direction thereto. The linear frame (106) prohibits uncontrolled movement of the detector head in any other direction relative to this linear displacement. The drive unit (107) for this displacement may be in the form of a translational responder for incrementally changing the position of the detector head (102) in the first plane P1 (radial movement) and for enabling scanning of radially adjacent subareas of a microfluidic disc device placed in the disc holder (105). Means II comprises the linear frame (106) and the drive unit (107) and is in FIG. 1 according to variant (2).

The drive unit (107) is associated with a unit (110) for determining the linear displacement and thus also the radial position coordinate of the part of the disc which is in front of the objective of the detector head (102). This unit (110) may be in the form of an encoder that gives a translational position and movement of the focal area (objective of the detector head) in relation to a translational home position (111) on the responder. This home position in turn may be associated with a unique radial position in the disc. The measuring unit (110) should be able to translate a translational position and movement of the detector head (focal area) into a radial position coordinate of the disc used with a high accuracy, typically within ±10 μm such as ±1 μm or ±0.1 μm.

The drive unit (107) and the vertical height of plane P1 may be adjustable for focusing purposes.

III. Controller

Control means, for instance electronic and programmable control means (schematically illustrated by reference numeral (112)) with operator's interface and software, not further disclosed, may be assigned to the detector arrangement among others for a) recognizing one or more pairs of start/stop-positions (angular and/or radial) for irradiating if the detection principle utilized requires irradiation and/or for collecting radiation,
b) identifying individual subareas in detection areas or elsewhere in the surface of the disc,
c) controlling the simultaneous rotating of the disc and the incremental radial displacement of the detector head (102),
d) collecting radiation data from the detection areas/detection microcavities,
e) treatment and presentation of the collected data, and/or
f) determining the time at which a particular angular position is in front of the objective of the detector head from the rotational speed,
g) storing and reading collected data in a data storage 130,
h) storing a computer program/computer program product, i.e., a computer software application in a computer software application and computer program storage 120, and reading and accessing software applications from the same.

The present invention may be implemented as a computer program product, i.e., a computer software application, directly loadable into an internal memory storage of a processing unit within the controller 120. Said computer program product comprises the software code means for performing the steps of the invented methods.

Further, the present invention relates to a computer program product stored on a computer usable medium, comprising readable program for causing a processing unit in a computer means, such as the controller 112, to control an execution of the steps of the invented methods.

The computer usable medium is a record medium, a computer memory, a read-only Memory or an electrical carrier signal.

Different parts of the arrangement may communicate (115) with the controller (112). The controller will in the preferred variants instruct the detector head to successively collect radiation from distinct and preselected parts of the surface of the disc. Typically, the controller is programmed to start collecting radiation at a position, primarily an angular and/or a radial position, which is prior to an intended detection area, and to stop collecting at a position, which is after the same detection area. The start and stop positions define a search area that at least should encompass the detection area or the relevant part of the detection area in which there is radiation from the substance. See further FIG. 4. If the radiation requires that the substance is irradiated, which is the case if fluorescence is measured, the control means also defines the settings for the start and stop positions for irradiation. These latter settings are typically essentially the same as for collecting radiation.

The start and stop signals for collecting radiation is preferably directly linked to the angular positions in the disc at which collection is to start and end, respectively. This also includes that due account is taken for delays that may be inherent in the system or preset, i.e., the start and stop signals may have to be initiated before the focal area is positioned in front of the start and stop position, respectively. If the angular aligning system comprises an encoder, the encoder signals corresponding to a start position and a stop position are used to define the time period during which radiation is to be collected. In an alternative, the start and stop for collecting radiation is linked to a preset rotating speed, i.e., the controller calculates from a preset rotating speed the time at which the start and stop position should be in front of the objective.

The controller may be programmed to change the radial position of the detector head (focal area) after a predetermined number of revolutions of the disc, for instance after 1, 2 or more revolutions with preference for 1.

The controller may be capable of changing the radial position of the objective (focal area) during a revolution of the disc. For these variants, one can envisage that radiation is collected for all relevant subareas at a common angular position before the disc is rotated (in a single step) to a subsequent angular position. In an alternative variant the objective (focal area) is transversing the disc surface in a spiral-like manner, i.e., the radial position is changed successively during a revolution.

In the preferred variants, the collected radiation data is stored in a data storage 130 in a form that is retrievable for each individual subarea, for instance in the control unit. This means that after collecting of radiation, it will be possible to represent the collected data as a 3-D image of each search area and/or detection area showing the amount of radiation from each individual subarea. In the case of overlapping subareas, the proper treatment of the data takes into account the overlapping effect and creates a true image of the radiation associated with different parts (subareas) of a detection area.

IV. Detection Principles and the Detector Head

The microfluidic devices used in the present invention typically require detection of very low absolute amounts or concentrations of substances in the detection microcavity. It is therefore imperative in many variants of the invention that the detection principle shall enable detection and quantification of substance amounts that are $\leq 10^{-12}$ mole per detection area/detection microcavity, such as $\leq 10^{-15}$ mole or $\leq 10^{-18}$ mole per detection area/detection microcavity.

Typical detection principles may include, for example, spectrometric detection, such as radioactivity, absorption of radiation (e.g., light), fluorescence, chemiluminescence, bioluminescence, scattered light etc. For variants in which radiation requires irradiation a change in wave-length(s), polarization, life-time, scattering, intensity, etc., between irradiation and radiation may be measured as a function of the presence of the substance of interest in the detection microcavity. Typical examples include, but are not limited to luminescence and fluorescence principles, with laser induced fluorescence (LIF) being preferred.

Details about the detector head are given in copending applications PCT/SE02/01678 and corresponding U.S. application Ser. No. 10/062,258.

Figure 2:
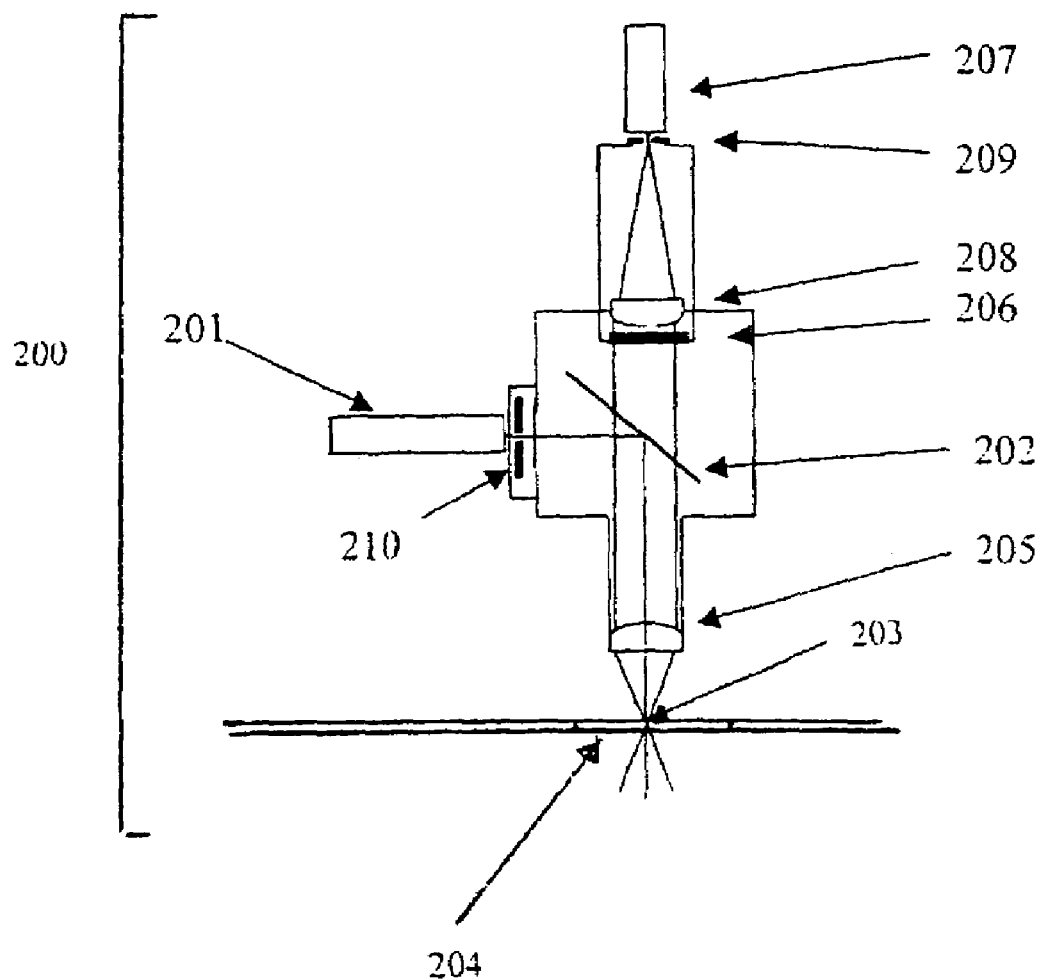
FIG. 2 illustrates a detector head placed above a disc (microfluidic device) (cross-sectional view).

The size of the focal area of the detector head typically is less than the size of a search and/or a detection area. The width of a focal area in one direction (direction 1) is typically essentially ≦⅕, such as of the ≦1/10, of the corresponding width of a search and/or detection area and in a perpendicular direction (direction 2) within the same limits or larger. A suitable detector head in the form of a pick-up head (200) is illustrated in FIG. 2 and comprises a laser source (201) whose beam is reflected on a dichroic mirror (202) and focused through an objective (205) to a part of a detection microcavity (203) positioned in front of the head. The epi-fluorescent light is passed through the dichroic mirror and through a band-pass filter (206), selective for the flourochrome at hand and is finally focused onto the entrance of a photo multiplicator tube (PMT) (207) by means of an aspheric lens (208). Pin-holes (209 and 210) are positioned between the entrance of the laser beam and the dichroic mirror, and in front of the PMT (207). The size and position of the pin-hole (210) are adapted so that the focal area of the laser beam is inside the detection microcavity. The size of pin-hole (209) is adapted so that preferentially emission light emanating from the focal area is passed into the PMT (207). A mirror spot on a glass disc or the like may replace the dichroic mirror.

V. Microfluidic Device

The microfluidic device used in the various aspects of the invention comprises a plurality of microchannel structures in which aliquots of liquids are transported and/or processed. The devices typically are disc-shaped. The structures are covered in the sense that their interior is in contact with ambient atmosphere primarily via separate inlet and/or outlet openings and/or vents. Each microchannel structure comprises one or more detection microcavities and possibly also one or more reaction microcavities, and microconduits connecting these parts with each other. A reaction microcavity may coincide with a detection microcavity. The result of the processing in a microchannel structure is measured as radiation from a detection area which is directly or indirectly associated with a detection microcavity.

A disc typically has an axis of symmetry ($C_n$) perpendicular to the disc plane where n is an integer ≧2, 3, 4, 5 preferably ∞ ($C_\infty$). The disc may thus be rectangular or have a circular shape.

Different principles may be utilized for transporting the liquid aliquots within the microfluidic device/microchannel structures. Thus inertia force may be used, for instance by spinning the disc (centrifugal force). Other forces are capillary forces, electrokinetic forces, hydrodynamic forces etc.

Microfluidic devices that have an axis of symmetry and are intended for rotation may have a home position mark as discussed above.

The terms "microchannel", "microconduit", etc., contemplate that a channel structure comprises one or more cavities and/or channels/conduits that have a cross-sectional dimension that is ≦$10^3$ μm, preferably ≦$10^2$ μm. The lower limit is typically significantly larger than the size of the largest reagents and constituents of aliquots that are to pass through a microchannel. The volumes of microcavities/microchambers are typically ≦1000 nl, such as ≦500 nl or ≦100 nl or ≦50 nl or ≦25 nl, which in particular applies to the detection microcavities. Chambers/cavities directly connected to inlet ports for liquids may be considerably larger, e.g., microchambers/microcavities intended for application of sample and/or washing liquids. Microformat means that one, two, three or more liquid aliquots that are transported within the device have a volume in the μl-range, i.e., ≦1000 μl such as ≦100 μl or ≦50 μl including but not limited to the nl-range (nanoformat), such as ≦1000 μl or ≦500 nl or ≦100 nl or ≦50 nl.

The microfluidic device may be made from different materials, such as plastics, glass, silicone polymers, etc. The detection area should be transparent/translucent for the detection principle utilized by the detector. From the manufacturing point of view plastic material is many times preferred because the costs for the material are normally low and mass production can easily be done, for instance by replication. Typical manufacturing processes involving plastic material are replication by embossing, moulding, etc., followed by attaching a top lid covering the open microchannel structures so obtained. See for instance WO 9116966 (Pharmacia Biotech AB, Öhman & Ekström). However, plastic materials may interfere with several sensitive detection principles. Their high auto-fluorescence is disadvantageous for normal fluorescence techniques in case low absolute amounts of fluorescent substances are to be measured. This points to the fact that it is important to match the material in the device with the detection principle used. At the priority date of this invention the preferred disc material is plastic material, such as polycarbonates and plastic material based on monomers which consist of a polymerizable carbon-carbon double or triple bonds and saturated branched straight or cyclic alkyl and/or alkylene groups. Typical examples are Zeonex™ and Zeonor™ from Nippon Zeon, Japan, with preference for the latter. See for instance WO 0056808 (Gyros AB, Larsson, Ocklind and Derand) which is hereby incorporated by reference. In this context silicone polymers such as poly dimethyl siloxane (PDMS) and the like are not considered to be plastic material.

It is known that black plastic material, for instance containing graphite powder or carbon black, absorbs light and therefore has a low auto-fluorescence. Transport of light within black plastic material is prevented. Black plastic material will be very efficient for microfluidic devices when fluorescence and luminescence measurements are relied upon. Black plastic material should in this case be avoided in the detection areas.

In case a lid is needed as for most discs obtained by replication, plastic lids of different origin may be used, for instance Melinex™ 12 PET and Melinex™ 17 OPP (Du Pont, U.S.A.), etc.

From the auto-fluorescent point of view an optimal combination of transparent plastic material appears to be Zeonor™ for replication and Melinex™ 17 OPP as the lid. This combination of material is likely to be useful for excitation wavelengths in the interval 480–650 nm.

The plurality of detection microcavities and the corresponding search and/or detection areas are preferably arranged in subgroups such that all members of a subgroup are positioned at the same radial distance and/or at the same angular position and/or have equal length and/or cross-sectional dimensions. Within each subgroup there may be at least two, three or more detection microcavities (detection areas), such as ≧10 or ≧25 or ≧50 detection microcavities (detection areas).

A detection area in the inventive arrangement typically has a size within the range of $1 \times 10^2 - 2 \times 10^6$ μm$^2$, such as $1 \times 10^3 - 10^5$ μm$^2$. Their length and/or bread are typically within the range of $0.5 \times 10 - 5 \times 10^4$ μm, such as $1 \times 10 - 10^4$ μm.

Design microchannel structures (301a,b,c, etc.) that are adapted to a circular disc are illustrated in FIG. 3. The structures are linked together by a common distribution channel (302) and a common waste channel (303). The orientation of the microchannel structures around a common axis of symmetry is apparent. The circumference (304) of the disc has a home position mark (305). Each of the combined reaction/detection microcavities (306a,b,c, etc.) is communicating in the downstream direction with the common waste channel (303) and in the upstream direction via separate connections with the common distribution channel (302) and separate volume measuring units (307a,b,c, etc.). A surface detection area (317a,b,c, etc.) is associated with each detection microcavity. The common distribution channel (302) carries at one of its ends and at an intermediary position inlet ports (308 and 309, respectively). Another kind of inlet port (310) is located at each volume measuring unit (307a,b,c, etc.). Each microchannel structure (301a,b,c, etc.) also has an outlet to the common waste channel (303) and an outlet port (318) at the remaining end of the common distribution channel (302). An inlet vent (311) to ambient atmosphere is connected to the common distribution channel via a common venting channel (312). Other vents (313 and 314) to ambient atmosphere are placed in the common waste channel (303) and in the connecting microconduit between each reaction/detection microcavity (306a,b,c, etc.) and the common waste channel (303). Appropriate valvings are positioned at 315 and 316 in each microchannel structure (301a,b,c, etc.).

The diameter of the preferred circular discs is about the same as conventional CDs but may be larger or smaller, for instance up to 300% or larger and down to 10% or less.

VI. Processes to be Preformed within the Microfluidic Device

The processes that are carried out within the individual microchannel structures comprise assay protocols, organo-chemical or biochemical synthesis protocols, etc. Typically the protocols comprise introduction of one or more liquid aliquots containing the necessary reagents/reactants into a microchannel structure. In the case of assay protocols, one of the aliquots is a sample which is uncharacterized with respect to at least one feature, e.g., type, form and/or amount of an analyte.

The processes comprises that the substance, which is associated with the radiation to be collected, is formed and/or retained in the detection microcavity under static conditions or under flow conditions. The reaction system for retaining may be homogeneous or heterogeneous, i.e., with or without the desired substance being partitioned between a liquid phase and a solid phase. In case of flow conditions and microfluidic devices in the form of discs, the flow direction in the detection microcavity may be towards the circumference (outwards) or towards the center of the disc (inwards), or essentially parallel with the circumference of the disc. Also other directions may be utilized.

Process protocols may utilize specific reactions between reactants having mutual affinity to each other leading to a (a) formation of an affinity complex that is immobilized to a solid phase in a detection microcavity or (b) one or more other reaction products that may be soluble or insoluble in the detection microcavity. By properly selecting the reaction conditions including selection of reactants, it can often be arranged so that the product obtained and/or a reagent in excess are detectable with a signal that can be (a) measured from the above-mentioned detection areas and (b) related to one or more features of a starting liquid aliquot introduced into a microchannel structure. Typical such features are kind, form and amount including activity, etc., of a particular reactant (e.g., an analyte) including for instance an affinity reactant such as an enzyme etc. The term "can be related to one or more features" includes also the determination of the manner in which reaction variables such as pH, ionic strength, detergents, etc., might influence the reaction used for forming the reaction product. Typically, one makes use of detection principles based on radioactivity, fluorescence, chemiluminescence, bioluminescence, enzymatic activity, chromogens, light scattering (turbidometry), etc., for instance by utilizing a reactant that carries a group providing detectability, either by being detectable as such or by being transformable to a detectable group. Typically the utilized process protocol means that a detectable reactant is incorporated into a complex or into some other reaction product. See for instance WO 02075312 (Gyros AB). Detectable products, reagents, etc., that can be formed and/or retained and measured in a microcavity via a detection area are collectively called "substance" in other parts of this specification.

Typical reactants in this context include members of affinity pairs such as (a) antigen/hapten and the corresponding antibody including its antibody active fragments, (b) lectin and the corresponding carbohydrate structure, (c) native ligands and the corresponding receptors, (d) complementary nucleic acids including synthetic variants such as synthetic oligonucleotides, (e) Ig(Fc)-binding proteins and Protein A, Protein G and other Ig(Fc)-receptors, (e) ion pairs of opposite charges, enzyme and the substrate, inhibitor, cofactor, coenzyme etc., that can bind to the enzyme, etc. Synthetic variants more or less mimicking a native affinity interaction are also included.

One aspect of the invention is a method and corresponding arrangement, for determining the amount of a substance in a detection microcavity of a microfluidic device and comprises collecting radiation associated with the substance from a detection area associated with the detection microcavity. The method is characterized in comprising the steps of:

a) providing
  (i) a microfluidic device, e.g., in the form of a disc, comprising
    A) a plurality of microchannel structures, each of which has an inlet port, a detection microcavity and a microconduit connecting the inlet port with the detection microcavity, and
    B) a plurality of detection areas and associated search areas as discussed elsewhere in this specification, each of the detection areas being (1) associated with one of said detection microcavities, (2) present in the surface of said device and (3) translucent/transparent for said radiation, and
  ii) a detector arrangement which is capable of collecting radiation from individual subareas of each of said search and detection areas;
b) processing one or more liquid aliquots in at least one of said plurality of microchannel structures so that the substance is retained in the detection microcavity of each of said at least one of said plurality of microchannel structures, provided that said substance and/or one or more reagents that are necessary for the substance to be retained in a detection microcavity are present in at least one of said one or more aliquots;
c) scanning the search and/or detection areas associated with the detection microcavities that are part of microchannel structures in which step (b) has been carried out to obtain radiation from individual subareas of each scanned search or detection area, said scanning being performed by the use of said detector arrangement;

d) integrating radiation as a function of the subareas of each scanned search area or detection area to obtain the amount of radiation from each search area or detection area;

e) characterizing for each of the amounts obtained in step (d) a reaction variable that has been included in the process protocol used for each microchannel structure.

Further details about characterization of reaction variables are discussed above and in WO 02075312 (Gyros AB). The characterization includes e.g., that the amount of the substance in absolute or relative terms in each of the detection microcavities is determined from each of the amounts obtained in step (d). The substance in this context may be the substance from which the radiation is directly derived or a substance, such as an analyte, the amount of which in one of the liquid aliquots used in step (b) is related to the amount of radiation determined in step (d). Since it is the result of the reaction that is measured the analyte may or may not be present in a detection microcavity after step (b).

Step (c) comprises collection of radiation intensities which refer to changes in the radiation due to the amount of a particular substance in the detection microcavity. This includes true intensity values but also other changes, such as changes in refraction, in scattering, in the plane of polarization and life time of fluorescent light (including half life, e.g.,), etc.

The microfluidic disc and steps (b) and (c) are illustrated elsewhere in this specification. In addition to circular scanning, e.g., by rotating a disc, step (c) also comprises non-circular scanning for instance scanning by lateral movement of a linear detector head comprising one or more rows of detector elements over the detection areas. Also imaging by a CCD camera is included. The microfluidic disc may be circular or have some other geometric form, for instance triangular, rectangular, etc., including also irregular forms.

Step (d) means integration over each detection area, i.e., primarily over subareas which have radiation values that deviate from the values obtained for surface parts of the device that surrounds the detection area. Alternatively one may exclude all or selected parts of a detection area which corresponds to parts of a detector microcavity in which the presence of the substance is insignificant. The integrating step includes the substeps of (a) finding a start and/or stop position at edges of the detection area, e.g., at an end corresponding to the inlet end of the detection microcavity, and (b) the factual integrating. In one variant substep (a) is carried out by determining the inflection point for the amount of radiation per subarea versus position along the detection area. Due the fact that the delineating part of the detection area may be curved, at the upstream end, the invention also suggests that the integration should account for curvatures in the circumference of a detection area. In a preferred variant, substep (a) comprises determining a threshold that segments detection area pixels from the background, e.g., if the detection microcavity is filled with a particle bed a threshold that segments the particle bed pixels from background pixels. This can be done with optimal thresholding or determining median or mean background or any other way of determining background (for "optimal thresholding" see for instance reference [1]: "Digital Image Processing", 2nd edition, Editors: Gonzales R C et al., page 354). In this case substep (b) means integrating a selection of pixels, i.e., those pixels which have radiation values above the threshold and belong to the main group (detection area) and excluding noise pixels above threshold that do not belong to the main group of connected pixels. The integrating typically starts from pixels corresponding to one end of the detection area, e.g., the inlet end.

Between the preferred variant of substeps (a) and (b), there are preferably additional substeps for refining the method, such as i) creating a binary image from the calculated threshold.

ii) labeling the high binary pixels into different groups (=labeling the image). Each group will consist of pixels that are bordering to each other (close to each other). The binary high pixels from the detection area defines the main group.

iii) optionally removing all binary high pixels that do not belong to the main group.

The factual integrating (main step d), in this case, means integrating the radiation values for the binary high pixels of the main group.

The inventors have found that when working with very small volumes and amounts, the material from which a device is manufactured as well as the pretreatment procedures may introduce radiation artifacts in form of peak noise that is comparable to the radiation coming from subareas outside the peak. Therefore step (d) may also comprise substeps for removing peak noise. This typically means a first substep in which the deviating radiation (peaks) are made more apparent. One way of doing this is 1a Place filtering, point detection and the like. See for instance see reference [1]: "Digital Image Processing", 2nd edition, Editors: Gonzales R C et al., pages 333, 334 and 339 (1987). In a subsequent substep the width and the position of each peak is calculated for instance by including edge detection or edge linking based on a local area etc. See for instance reference [1]: "Digital Image Processing", 2nd edition, Editors: Gonzales R C et al., pages 334 and 344 (1987). In the next substep the peak noise is removed by interpolating from surrounding subareas. An alternative way to the whole process of removing peaks is morphological opening, un-linear filtering operating in local histogram domains etc. These substeps for removing peak noise is performed prior to the factual integration.

Step (e) is conventional and typically includes that the integrated value is compared with the value for one or more standards. A standard value is typically the integrated value for a known amount of a standard substance, which in most cases is the same as the substance under investigation.

The scanning step (c) and integrating step (d) may in certain innovative variants of one aspect of the invention be optional. Thus, these steps are preferably included when the desired substance is unevenly distributed within the detection microcavity. In a typically case, this may happen when the substance is retained within the detection microcavity under flow conditions, for instance by being captured to a solid phase introduced into the microcavity prior to the fluorescent substance.

In the case that the substance is homogeneously distributed within the detection microcavity, the scanning step (c) and integrating step (d) may be replaced with collecting the radiation intensities for selected subareas of a detection area and letting these intensities represent the total amount of radiation from the detection area, for instance as a mean or maximum value. Step (e) can then be carried out on these values in the same manner as for values obtained by scanning and integrating. This way of performing the method is also a part of the present invention.

Homogenous distribution of the substance in the detection microcavity typically is at hand in case the substance is present in the detection microcavity in an equilibrated solution and/or when a reaction is going in the microcavity between homogeneously distributed reactants either forming or producing the substance that is to be detected.

The innovative method of the aspect discussed in the preceding paragraphs includes that steps (d) and/or (e) are performed in close connection to the preceding steps [(a)–(c) or (a)–(d), respectively] and/or that the data from the scanning and/or the integrating have been obtained at an earlier time, for instance at a different geographical location, and/or by different individuals.

Steps (d) and (e) in the method for determining the amount of a substance that is associated with the collected radiation as well as any of the other individual method steps or their combinations discussed are typically performed by the appropriate software for instance included in the controller or elsewhere, for instance not in physical association with the innovative arrangements described herein.

The invention also comprises computer program-related aspects for treating radiation data that have been assembled by steps (a)–(c) of the innovative method. One such aspect is a computer program product that (1) comprises program code elements corresponding to a sequence variant of step (d) above comprising one or more of the substeps described for this step, and (2) when installed on the appropriate hardware is capable of causing the hardware (computer) to execute the sequence of substeps on data which have been obtained by performing step (c) above on any kind of microfluidic device irrespective of being spinnable or not.

Other code elements may be included, for instance corresponding to step (e) in order to execute the sequence (d)–(e). Another computer program-related aspect is the computer program product stored at a computer program readable means which, when the product is loaded, makes it possible for a computer to perform the sequence of steps corresponding to the code elements in the stored computer program product. A third computer program-related aspect is a carrier having at least one of the innovative computer program products thereon. The carrier may be a computer memory, a read-only Memory or an electrical signal carrier.

The present invention may be implemented as a computer program product directly loadable into an internal memory storage of a processing unit within the controller in the detector arrangement, comprising the software code means for performing any of the steps described herein.

Further, the present invention relates to a computer program product stored on a computer usable medium, comprising readable program for causing a processing unit in a computer means to control an execution of any of the steps described herein.

The computer usable medium is a record medium, a computer memory, a read-only memory or an electrical carrier signal.

VII. Method for Reducing Noise in a Substance Raw Data Image Containing Noise

In the described method for determining an amount of a substance in a detection microcavity of a microfluidic device, it may be necessary to reduce the noise contribution in the detected radiation intensity from scanning step (c) in the integration step (d).

An algorithm, or rather an automated method, for that is detectable by use of a particle bed is presented hereinafter. This algorithm may be started for each scanned search area/detection area/particle bed of interest.

The invention will now be further detailed with respect to a particular example comprising a microfluidic device (see FIG. 3) in a disc format, comparable to Compact Disc (CD), having an axis of symmetry perpendicular to the disc plane and with a radial flow direction from the axis of symmetry for each of the detection microcavities (see FIG. 3: reference number 306a,b,c, etc.) that comprises a bed of particles. This kind of microfluidic device will henceforth be called CD. The signal detected and measured may be fluorescence from an antibody fluorochrom conjugate (antibody-fluorochrom). Each bed defines a detection area (see FIG. 3: reference number 317a,b,c, etc.) in the surface of the disc. See for instance WO 02075312 (Gyros AB). The detection area is part of a search area comprising also a defined minor zone around the detection area. The principles outlined in this example may be adapted also to other devices. The principles are also applicable to other kinds of radiation as discussed elsewhere in this text.

As described in section III, Controller, of this description and incorporated herein, a controller means (FIG. 1: ref. No. 112) is programmed to control the scanning and detection.

Each search area is scanned by a detector head that is capable of detecting a detectable physical feature deriving from a substance present in the microcavity, like radiation caused by radioactivity, fluorescence, chemiluminescene, bioluminescence, enzymatic activity, scattering of light, absorption of light, reflection of light, etc. The measured data are stored in a data storage, an image data storage, connected to or connectable to an processing unit, which may either be comprised in the controller means, or as in another possible embodiment, incorporated in a separate computer system. Each search area is identified by an identifier, which may be used as address. The identifier makes it possible for the system and controller means to locate each single search area and its detection area on a CD and link the corresponding stored measured data in the image storage.

Figure 4:
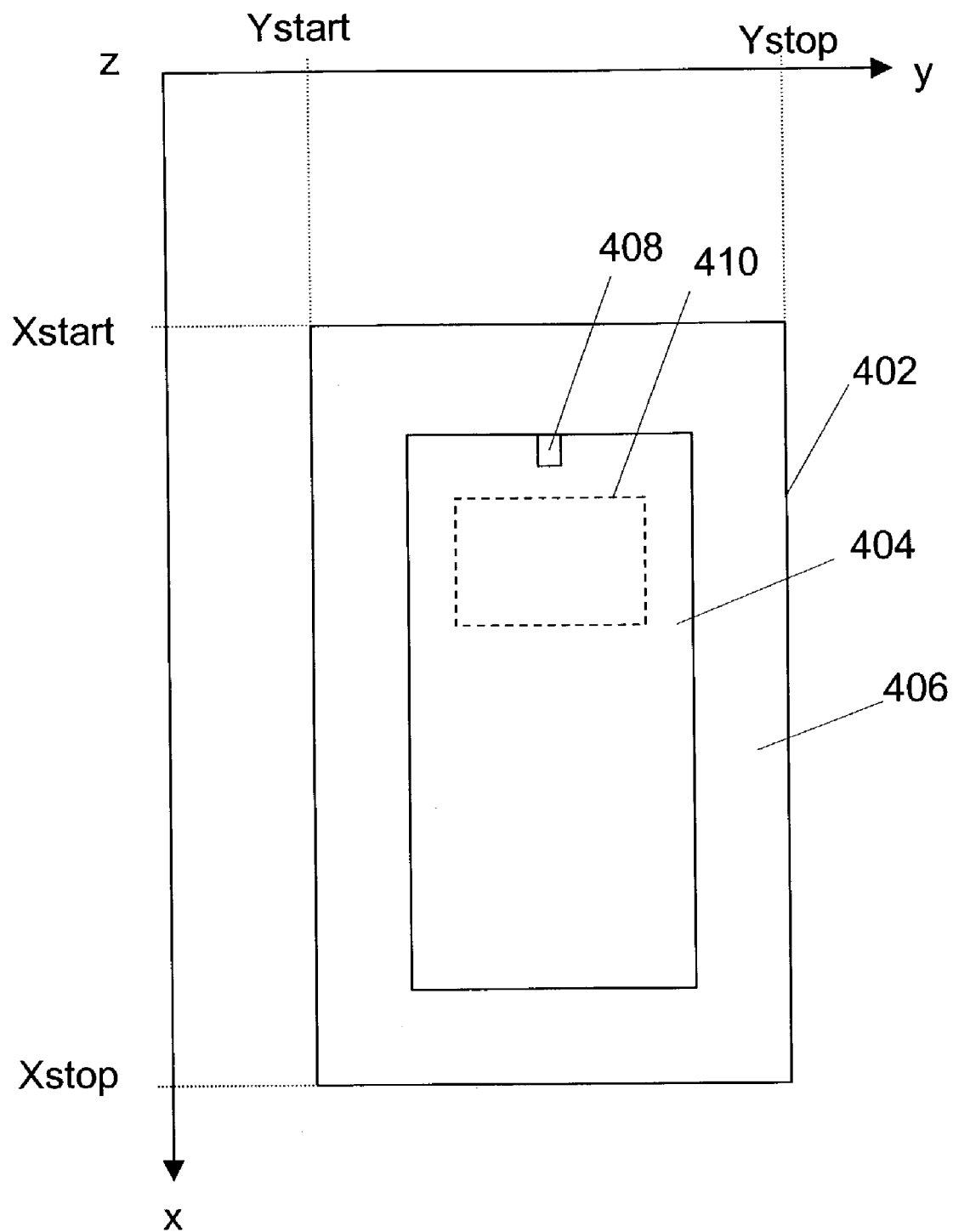
FIG. 4 illustrates the search and detection areas.

Now with reference to FIG. 4, each search area 402 has a pre-defined radial start position, Xstart, a pre-defined angular start position, Ystart, a pre-defined angular stop position, Ystop, and a pre-defined radial stop position, Xstop. The start of the collecting of data is started at a position, primarily an angular and/or a radial position that is prior to an intended detection area, and to end the collecting at a position that is after the same detection area. The search area will therefore cover an outer area 406 surrounding the detection area 404. The search area 402 is scanned in radial direction by the detector disc lap by disc lap. The radial start position Xstart is the number of disc laps/revolutions, counted from a spinning start position, Spinstart (not shown). When the scanning of a search area starts, and the radial stop position is the number of laps, counted from the spinning start position, when the last angular scanning of the search area is to be performed. The scanning of the search area in the angular direction starts during the lap, which is defined by the radial start position, at the angular start position in the angular direction, which is defined by the spinning direction of the disc and the detector position in relation to a Home Mark on the CD. The scanning in angular direction is stopped at the angular stop position.

FIG. 4 is schematic in the sense that the search area of a rotatable device typically is a) slightly narrowing when going from an outer position inwards towards the centre of the CD, and b) slightly arc-shaped. Compare for instance that the Ystart position for each lap are always at the same angular position (which also applies to the Ystop position).

During a lap, from the angular start position to the angular stop position, a stream of collected data from that search area will generate a corresponding stream of measured data that are stored into the storage. This is repeated lap by lap from the radial start value to the radial stop value. The processing unit of the controller 120 links measured data to the correct identified detection area, and there will be no mixing of measured data from different search and/or detection areas. Each scanned search area has a corresponding set of collected measured data. The processing unit will organize the data in such an order, position by position in each set of measured data, and it is therefore possible for the image processor to locate a certain measured value in the set. The set of measured data has therefore similarities to an electronic and/or digitally stored image. An image is defined in very small elements, called pixels. Each pixel corresponds to a position of a measurement area in the search area.

When the scanning, detecting and storing are finished, the measured data of a search area is possible to plot by use of printer/plotter software program used by the processing unit in a three dimensional diagram, wherein the horizontal plane is defined by the two dimensions x and y, in this case the radial direction, x-axis, and the angular direction, y-axis, which is perpendicular to the x-axis. Positive x-direction is defined as the main flow direction (downstream) through the detection area, from the inlet 408 of the detection area 404 to the outlet of the same. Positive y-direction is defined as the scanning direction which is orthogonal/perpendicular to the radius (or flow direction). The third dimension, z-axis, perpendicular to the horizontal plane defined by the x- and y-axis, is the magnitude of the measured value, e.g., measured value of the fluorescence intensity. The measured data defines a surface of measured data, having peaks and valleys. As mentioned above, the three dimensional figure has essential similarities with an image having an intensity value defined for each pixel, and the surface of measured data is therefore called an image of a search area/detection area/particle bed comprising the substance from which the measured signal derives. In the description of this application, an image is the stored detector measurement data belonging to a search area/detection area/particle bed. A pixel is here defined as a discrete measurement area within the search area/detection area and each pixel may have a measured intensity value, a pixel value. The resolution of the image is depending of the number of discrete measurement points in the y-direction and the number of laps in the x-direction within the search area. The resolution increases with increasing density of measure points and scanning laps, and consequently, the area of a pixel will decrease. If the electromagnetic-emitting source is a laser, the possible minimum pixel area is limited by the minimum cross-section of the laser beam with the search area.

During the scanning of the search areas the pixel intensities are determined by the detection process and stored as digital pixel data representing raw data images of the search areas.

The space between the surface of measured data for the search area/detection area and the base plane, defined by the two axes in the base plane, constitutes a volume. The whole or a part of the volume may represent a wanted measure for a chemical process, i.e., a reaction variable. This value is possible to calculate by using a mathematical method, e.g. addition or integration of measurement data over the whole area of the detection area, or one sub-area 410 (FIG. 4) or a number of sub-areas of the detection area. Sometimes the object is to calculate an amount for an subarea, here called a normalized area, i.e., a predefined amount of pixels, inside the detection area. This is done to minimize the variance between detected structures. The variance depends among other things on background radiation, such as fluorescence, from the detection area.

In an ideal image of a detection surface, the area is smooth, because of the absence of noisy background contribution in the measured raw data signals from the detector. This image includes only measured data from a substance signals, i.e., the substance contribution to the detected and measured raw data signal. In reality, a substance raw data image comprises measured substance data and noise data. The noise cause irregularities, like noise peaks, in the surface, and evidently, a calculation of the volume in an area having one or many noise peaks will not result in a true measure for a chemical process.

It is therefore necessary to reduce the noise contribution in a substance raw data image as much as possible before calculation of the measure.

The present invented method provides a method for reducing noise contribution in a substance raw data image derived from a detection area of a microfluidic device of the kind described above. The method comprises a number of main-steps for reducing different kind of disturbances and noise within an image.

The method removes noise from substance raw data information in substance raw data images. Each image is associated to one detection microcavity and one substance that is present in the detection microcavity of a microfluidic structure of a microfluidic device. The substance raw data information is obtained by use of a detector arrangement capable of scanning a search area associated to a detection area, which is associated to the detection microcavity. The detector arrangement is capable of detecting at least one of a number detectable physical features discussed above, e.g., fluorescence, luminescence, etc., emitting radiation from the search area, and generate output that is proportional to the magnitude of detectable activity. The output is converted to measure data storable as substance raw data in a set in a data storage. The method may comprise following steps in any order for removing different noise signals contributions step-by-step in any order in a substance raw data image:

reducing background radiation (step $\alpha$);

reducing peak disturbance (step $\beta$);

locating the detection area within the search area (step $\chi$);

moving binary artefacts (step $\delta$);

removing unwanted areas of the detection area (step $\epsilon$); or applying default detection area in noisy images (step $\phi$).

Each of the steps $\alpha$–$\phi$ comprises a number of sub-steps. Steps $\alpha$–$\phi$ may be regarded as an algorithm, but is not necessary that all of the steps $\alpha$–$\phi$ are carried out for all images. The order and kind of steps is typically preselected and depends among others of the sensitivity and accuracy required in each individual step. In general, inclusion of more steps is required when high sensitivity is desired.

Figure 5:
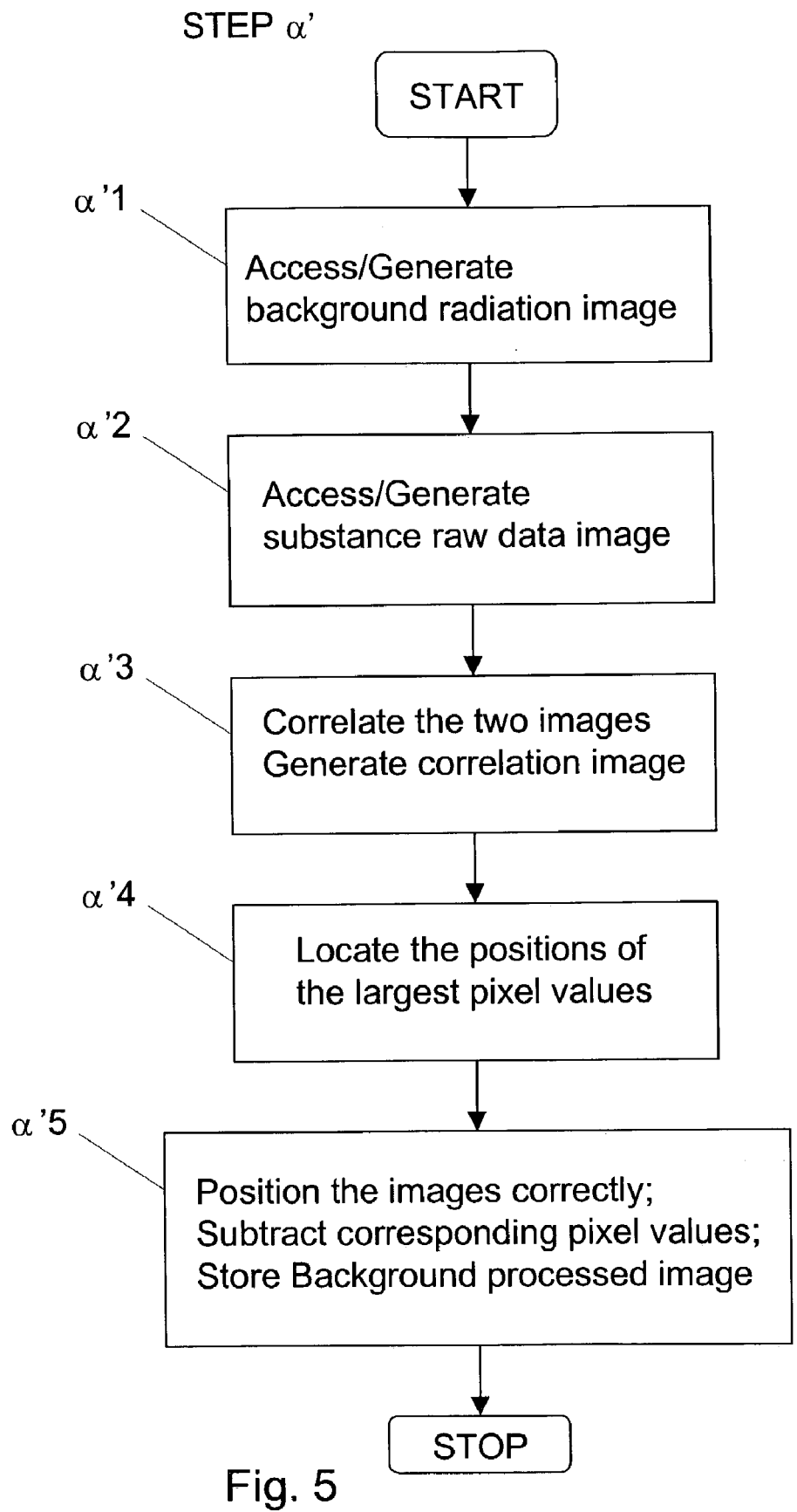
FIG. 5 is a flow chart illustrating a first variant, $\alpha'$, of a method step $\alpha$ according to the invention.

A. Step $\alpha$: Reducing Background Radiation and Construction of Background Processed Images The object is to remove the electronic, optical and dust noise that may be visible in the image. This part of the invented method mainly comprises two variants. In the first variant, a background radiation image is used. In FIG. 5, the first variant is presented schematically in a flowchart. Following steps may be used:

if available, accessing a background radiation image or, if not available, generating a background radiation image (step $\alpha'1$);

if available, accessing corresponding substance raw data image or, if not available, generating substance raw data image (step α'2);
correlating the two images and generating a correlation image (step α'3);
locating the positions of the largest pixel values (step α'4);
positioning the images correctly, subtracting corresponding pixel values and storing the generated background processed image (step α'5).

In the first variant, the first step, step α'1, is to scan the disc and measure the radiation, e.g., the intensity of the fluorescence, without presence of the substance giving raise to the measured signal from the detection areas, e.g., before step b) in the method for determining the amount of a substance, retaining the radiation associated substance before the detection areas/particle beds of the disc have been treated, e.g., with antibody-fluorochrom. All search areas/detection areas are scanned and each of the corresponding sets of measured data is stored in a background radiation image. When using antibody-fluorochrom, the corresponding image is called background fluorescence image. The image contains the measured data of the background radiation noise signal and other noise signals. In preferred variants the scanning for the background radiation image is carried out as close as possibly to the step in which the substance causing the radiation is formed and/or retained in the detection microcavities. Although not preferred, the manufacturer may provide a background radiation image that for instance may be based on the average of many CDs of the same kind.

The second step, step α'2, is in this first variant the same as step c) in the method for determining the amount of a substance, above. The substance is now present in the detection microcavities, for instance retained in particle beds that may have been washed, e.g., after the particle beds have been treated with e.g., antibody-fluorochrom. This image is the substance raw data image, described above.

If the background radiation images and corresponding substance raw data images exist already and are availably stored, there is consequently only to access (e.g., by copying or reading) the images in step α'1 and step α'2 instead of generating them again by the scanning and detecting processes.

The two images should be detected under the same conditions, e,g., same laser power and same detector sensitivity if the detection principles is based on fluorescence.

The third step of the first variant, step α'3, is to correlate the two images in two dimensions, that define a correlation image, by use of a two-dimensional correlation. The use of two-dimensional correlation is well-known in the art of signal-processing, see reference [1], page 90–92. Thus, the step has resulted in a correlation image.

In the fourth step, step α'4, of the variant, the position of the pixel, or pixels, having the largest intensity value in the correlation image is/are located. This could be done by using a simple comparison algorithm, wherein the recently largest value is stored and compared with the next data, e.g., intensity value, that hasn't been compared with any of the earlier pixel data. The positions of the pixels having the largest pixel values, largest intensity values, are stored and used in the next step, step α'5.

In step α'5, the background radiation image is moved to the correct position of the correlation image by using the identified pixel positions. The parts of the image that overlap is subtracted pixel by pixel.

These five steps have resulted in a new image, the background processed image.

The substance raw data image comprise the wanted substance radiation data. If not any new noise have been introduced by the introduction of the substance giving rise to the measured signal into the microcavities (part of step b), the process of noise removing may be stopped.

Figure 6:
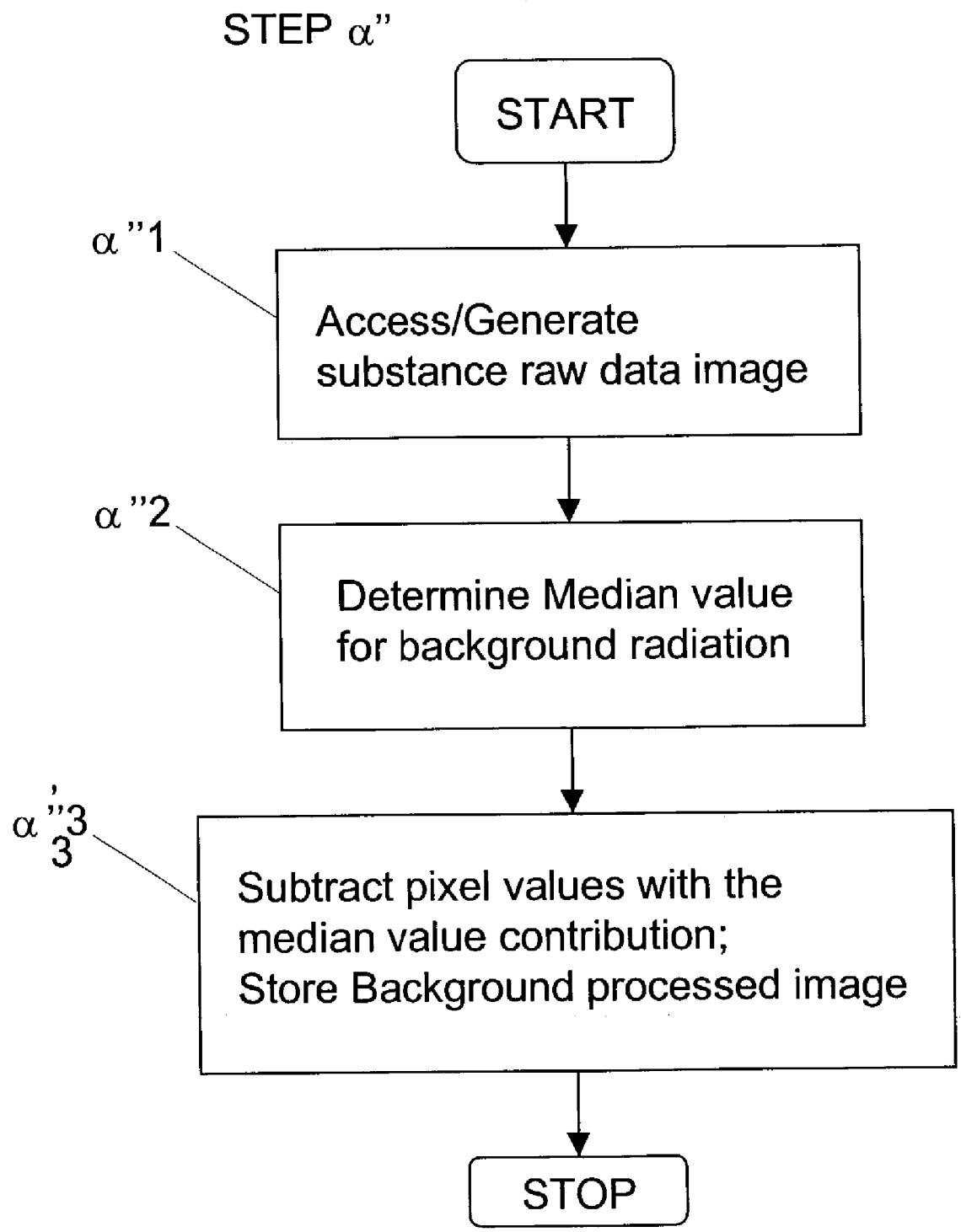
FIG. 6 is a flowchart illustrating a second variant, $\alpha''$, of the method step $\alpha$ according to the invention.

In the second variant is a Median value of the background radiation data used. In FIG. 6, the first variant is presented schematically in a flowchart. Following steps may be used:
accessing or generating a substance raw data image (step α"1);
determining a Median value for background radiation data (step α"2);
subtracting pixel values of substance raw data image with the median value, and storing the background processed image (step α"3).

The second variant of reducing background radiation and construction of background processed images is described in more detail. This second variant for removing background radiation, like fluorescence, especially for removing electronic and optical noise that exists in the search area outside the detection area, is possible to use instead of the five steps described above. This alternative variant works very well under the condition that there is no unwanted object of large size outside the detection area and the background signal intensity is constant inside the image. This variant has the advantage that the disc is scanned only once, which is described hereinafter.

The first step, step α"1 in this alternative variant, should start after the radiation associated substance has been incorporated into the detection microcavities. In the method for determining the amount of a substance above this for instance corresponds to after the detection areas have been treated with the antibody-fluorochrom, i.e., in step c. As described above, during the scanning of the search areas for the radiation, the pixel values of the substance raw data images are detected and determined, and stored as digital pixel data. If the substance raw data images exist already and are availably stored, there is consequently only to copy/read the images, instead of generating them again by scanning and detecting processes.

In the second step, step α"2, a median value of the pixel values for at least a portion of the search area outside the detection area is calculated and used as background radiation value, e.g., as a value for the background fluorescence. The median value is an estimated value for the background radiation (intensity).

In step α"3, the substance raw data is decreased with the median value contribution, e.g., by subtraction, pixel by pixel, until all pixels are processed and a background processed image is provided.

Potentially the step for determining Median value may be replaced by determining some other form of an average value and use this value instead of the Median in the subsequent steps.

Both methods, α' and α", provide a background processed image for each scanned search area, i.e., an image with reduced background radiation, such as fluorescence, and can be used separately or in combination in other steps of the innovative method, with the former being preferred at the moment.

B. Step β: Reducing Peak Disturbances

The method of this aspect of the invention may comprise one or more steps in which peak disturbances originating from dust, chemistry and other artefacts are reduced, e.g., reducing peaks from fibres. The disturbance peaks have typically a relatively high amplitude and a relatively narrow distribution. However, the image of an ideal detection area is smooth and does not contain any disturbance peaks.

Figure 7:
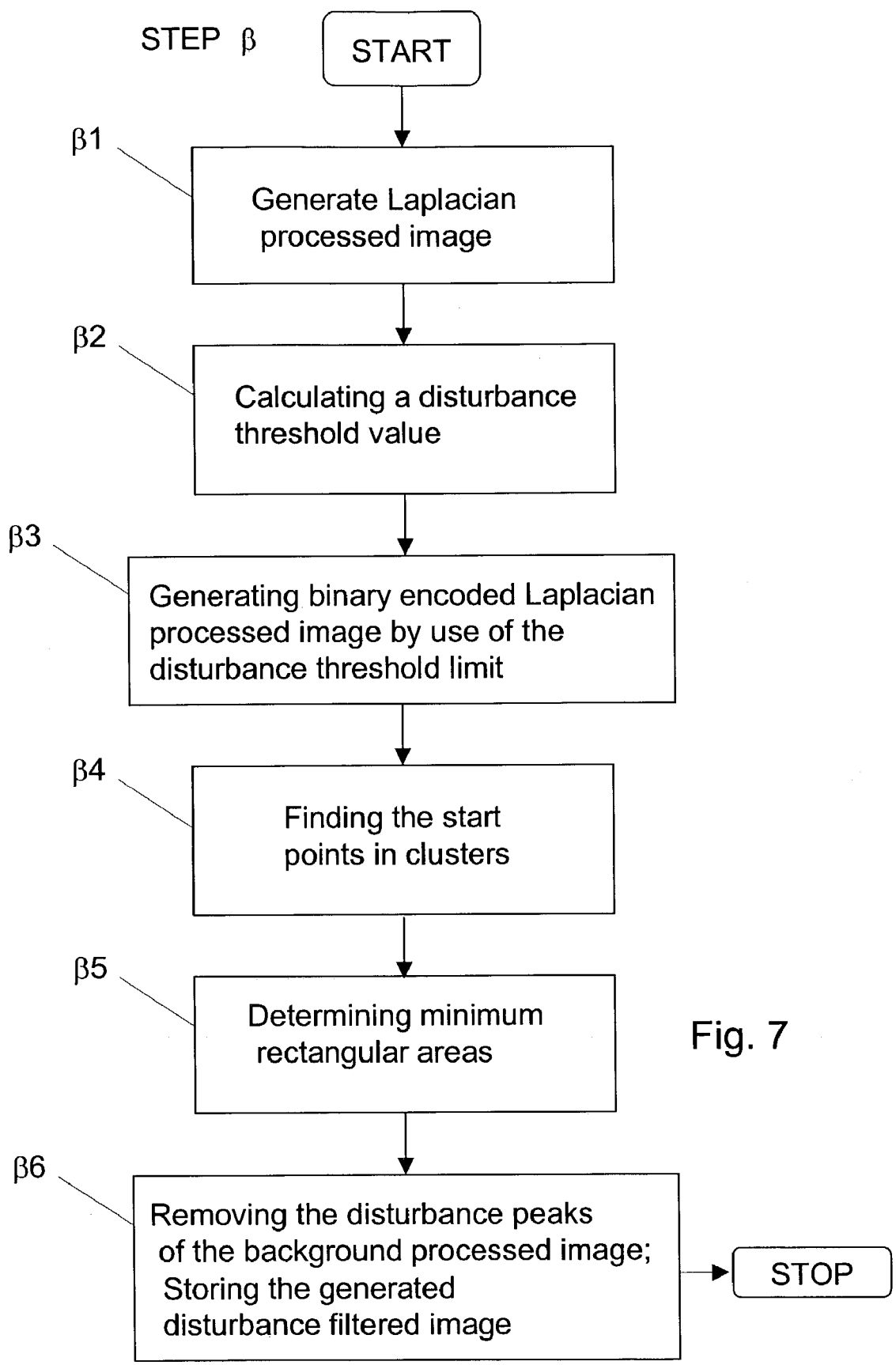
FIG. 7 is a flowchart illustrating a second variant, $\alpha'''$, of the method step $\alpha$ according to the invention.

In FIG. 7, step β for reducing the peak disturbances is presented schematically in a flowchart. Following steps may be used:

- generating a Laplacian processed image from the earlier stored image, typically a background processed image, by using a Laplacian filter in two dimensions (step β1);
- calculating a disturbance threshold value from the image created in the previous step, typically from a background processed image (step β2);
- generating binary encoding Laplacian processed image by applying the disturbance threshold limit to the image used for calculating the threshold value (step β3);
- finding the start points in clusters (step β4);
- determining a minimum rectangular area surrounding the start points (step β5);
- calculating an interpolated value within each peak area and substituting the original data of the peaks, and storing the disturbance filtered image (step β6).

Thus in a first step, step β1, a radiation intensity image, for instance a background processed image as discussed above, may be processed by a Laplacian filter in two dimensions. This is a standard method earlier known from reference [1]. The result of this step is that peaks in a background processed image are amplified. The result is normalized with the maximum radiation (intensity) in the background image. This step provides a Laplacian processed image.

In a second step, step β2, a disturbance threshold limit is calculated by use of the standard statistic functions average and standard deviation of the stochastic background noise, calculated from the image used in step β1. This step enhances the disturbance peaks of the image.

In the third step, step β3, the Laplacian processed image is binary encoded. In the encoding process pixel intensities/values equal to or higher than a threshold limit are set to one of the two corresponding binary values, for instance "1" or "positive" and pixel intensities less than the disturbance threshold limit are set to the other of the binary values, for instance "0" or "negative". The determined disturbance threshold limit determined in step β2 may be used in step β3 for encoding. This step creates an image wherein the high intensity pixels of the peaks appears as groups, even called clusters.

In a fourth step, step β4, the Laplacian processed image may then be processed for finding the pixel in each peak having the largest value by using the position information from the clusters in the binary Laplacian processed image. Each pixel having the largest value in a cluster is defined to be a center and start point. The other pixels of the clusters are set low in the binary Laplacian processed image. This step results in a cluster image.

In a fifth step, step β5, the start points defined in the cluster image is used for determining a minimum rectangular area by iterative testing using different area sizes. The iteration, that works on the Laplacian processed image, is stopped when a minimum rectangular area contains only pixels having a negative intensity value or zero value according to the definition in previous steps and as a result of the earlier performed Laplacian filtering. Said pixels surround the corresponding start point and defines the position, the area of the corresponding disturbance peak and the boarder pixels which is outside the peak area.

In a sixth step, step β6, the disturbance peaks of the background processed image are removed by substituting the original data within each peak area with an interpolated value between the boarder pixels of the corresponding peak. The interpolated values are calculated by use of an appropriate interpolation function, both a linear and a non-linear function is a possible choice.

The process has now generated a "disturbance filtered image" of the radiation intensity, e.g., fluorescence intensity, of the detection area.

C. Step χ: Determining a Global Threshold Value

The object of this part of the invention is to make a radiation intensity image, such as a disturbance filtered image, binary by determining a global threshold that separates the measured substance signals, i.e., the signals from the substance in the detection area, from the background signals. For instance, the detection area pixels should be equal to binary high, like "1", and the rest of the image equal to binary low, like "0".

The purpose of the following steps is to determine a valid global threshold value. This is done by an iteration that tests different threshold values. A global threshold is valid when only a few pixels in a part of the search area that is not connected to the detection area have an intensity higher than the pixels in the detection area.

Figure 8:
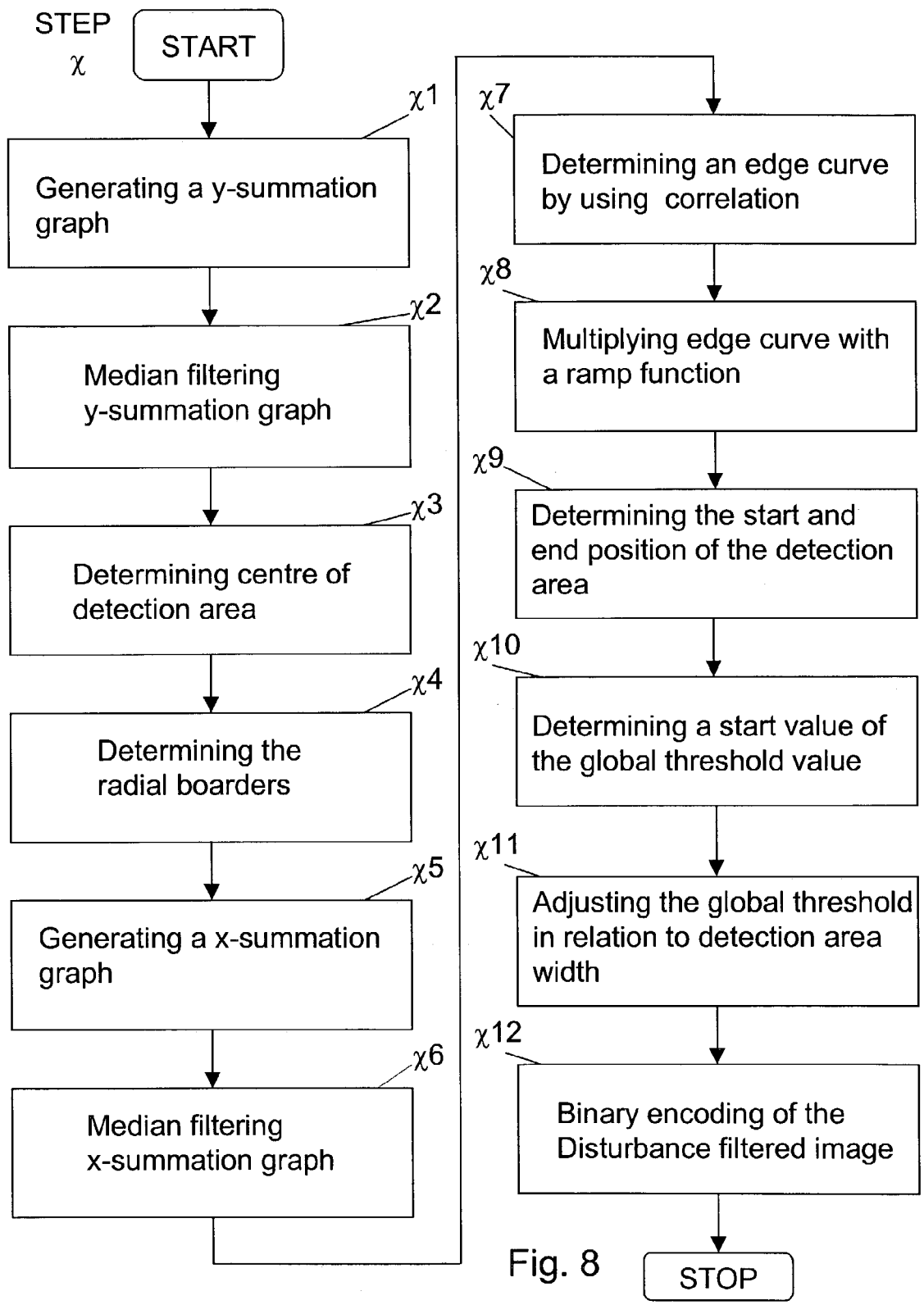
FIG. 8 is a flowchart illustrating a method step $\chi$ according to the invention.

In FIG. 8, step χ for determining a global threshold value is presented schematically in a flowchart. Following steps may be used:

- generating a y-summation graph (step χ1);
- median filtering of the y-summation graph (step χ2);
- determining centre position of detection area (step χ3);
- determining radial directed edges of detection area (step χ4);
- generating a x-summation graph (step χ5);
- median filtering of the x-summation graph (step χ6);
- determining an edge curve (correlation) (step χ7);
- restraining disturbance peaks in the edge curve (step χ8);
- determining the start and end positions of the detection area (step χ9);
- determining a start value of the global threshold value (step χ10);
- adjusting the global threshold value to the value giving correct detection area width (step χ11);
- generating a binary encoded disturbance filtered image by use of the global threshold value (step χ12).

In a first step, step χ1, pixel values are summarized in the radius direction, pixel values, line by line, in a radiation intensity image, typically the disturbance filtered image, to get a one-dimensional y-summation graph in the y-direction of the radiation intensity, e.g., fluorescence intensity (angular direction on a spinning disc). Each y-coordinate on the graph will be the sum of the pixel values in radial direction having the same y-coordinate.

In a second step, step χ2, the y-summation graph is filtered to remove disturbing peaks, e.g., with a median filter function.

In a third step, step χ3, the centre of the detection area in y-direction (angular direction on a spinning disc) is calculated and located by use of a correlation, and with the filtered y-summation graph and the known detection area width as input value to the correlation length. This should normally give a graph with one large peak.

In a fourth step, step χ4, the centre of the largest peak is set to the centre of the detection area. It's now possible to calculate the positions and the radial extension of the particle bed edges by use of the known data for the centre and detection area/particle bed width. Hereby, the radial directed boarder/edge pixels are known.

In a fifth step, step χ5, the radiation intensities are summarized in the image in y-direction (angular direction on a spinning disc) using the limits (boarders) determined in the previous step to get a x-summation graph (radial summation graph) in x-direction (radius direction) of the radiation intensities. The summation of pixel values is performed in the same way, but in the orthogonal direction in the same plane, as in step $\chi 1$.

In the next step, step $\chi 6$, the x-summation graph is filtered with a median filter function to remove disturbing peaks.

Figure 9:
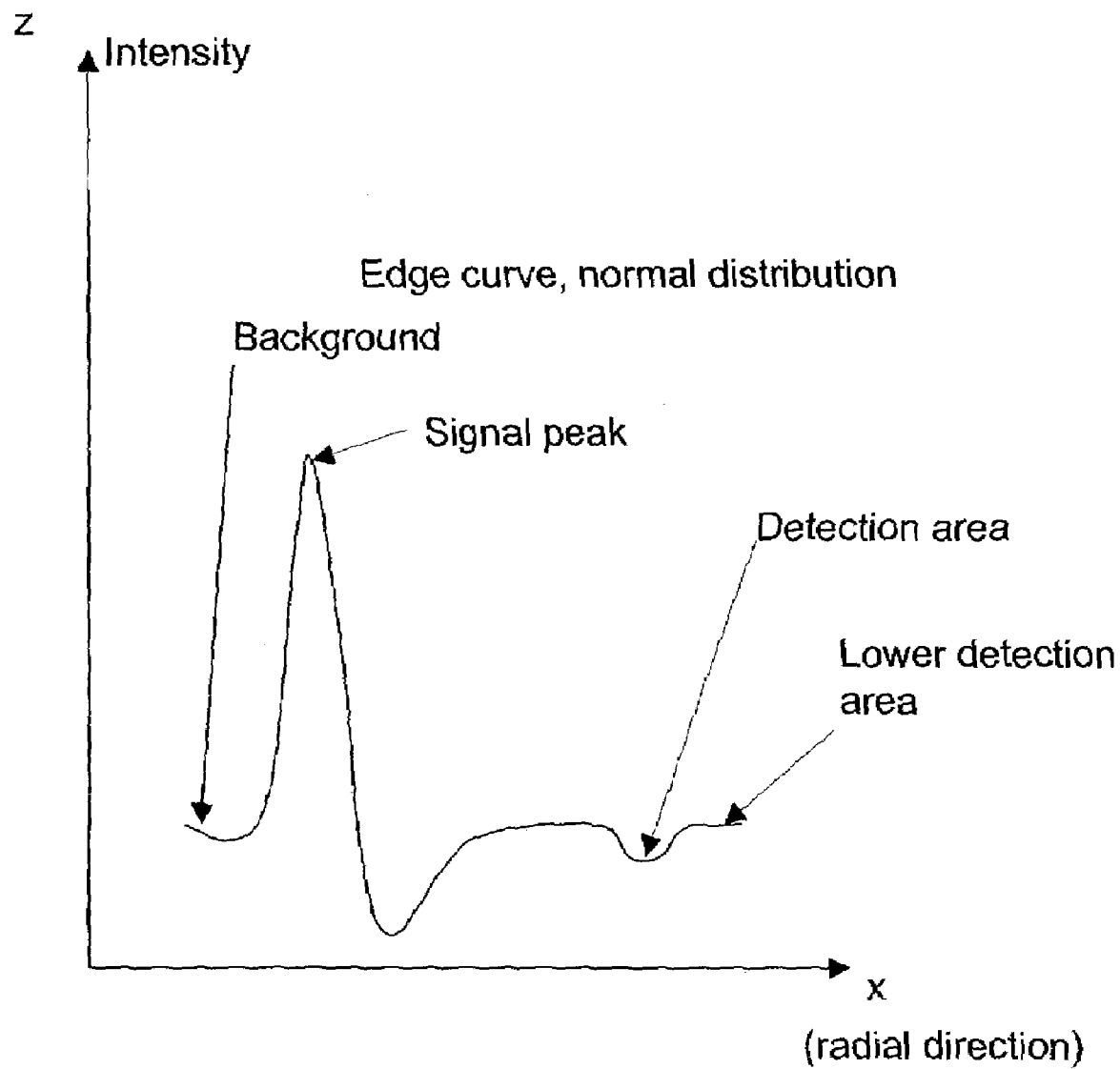
FIG. 9 illustrates an edge curve.

In the seventh step, step $\chi 7$, the start of the detection area in the x-direction is determined by use of correlation between a step function and the filtered x-summation graph. The mathematical process results in an edge curve, see FIG. 9.

In step $\chi 8$, disturbance peaks, close to edge that is sitting opposite to the inlet, are restrained by multiplying the edge curve with a ramp function.

The purpose of step $\chi 9$, is to find the start position of the detection area by finding the highest positive peak centre in the filtered edge curve (from step $\chi 8$) and using a minimum detection area length to calculate the end position of the detection area.

An approximate position of the detection area edges, boarder pixel is now known.

Figure 13:
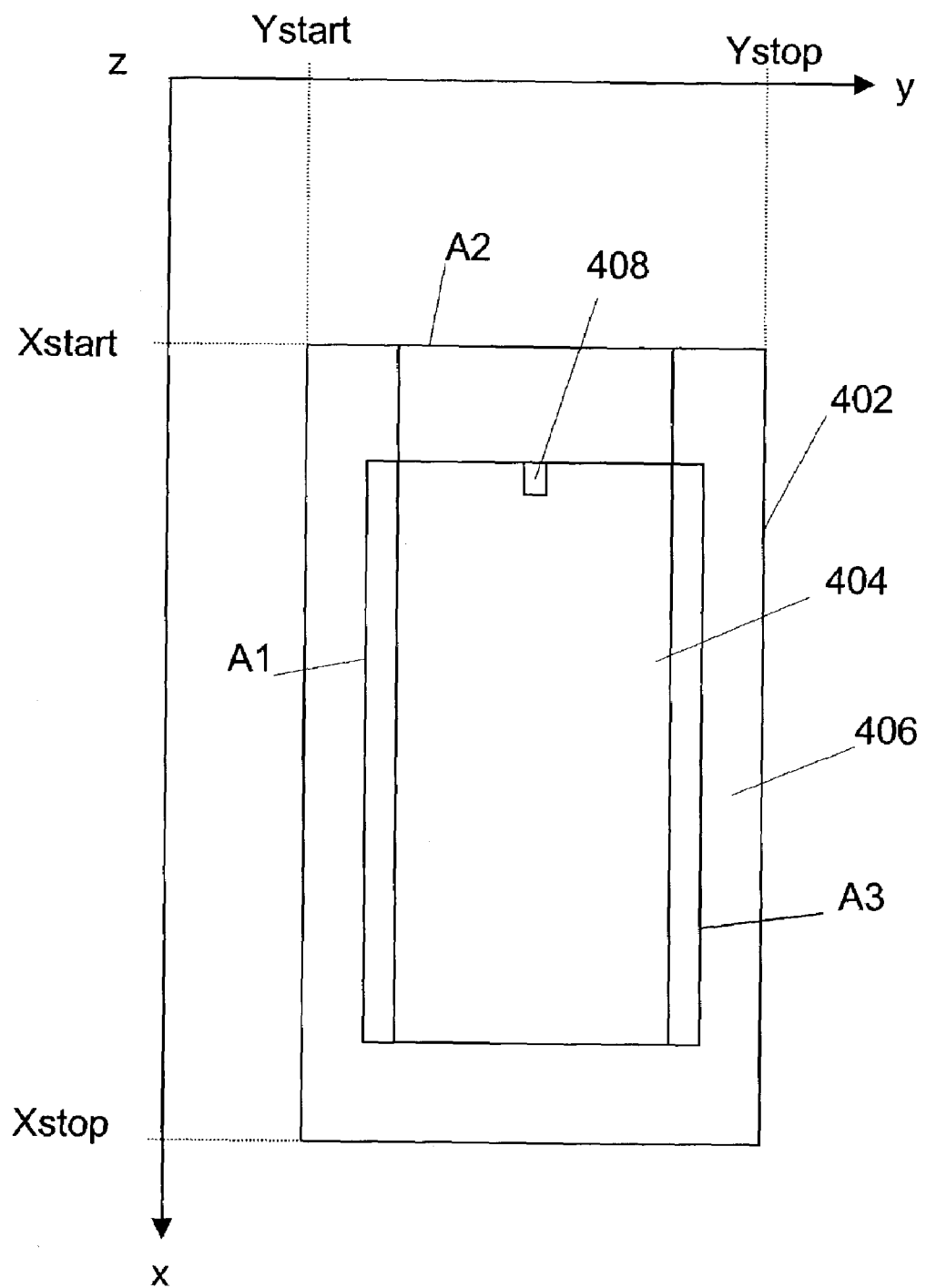
FIG. 13 illustrates the search and detection areas and the surrounding areas A1–A3.

In the tenth step, step $\chi 10$, the global threshold value is now determined by use of optimal threshold technique for image processing (reference [1], starting at page 360). It is assumed that the background and particle bed peaks are normal distributed with the same variance. Calculate from the disturbance filtered image the estimated background intensity as max of (median background intensity on the areas A1+A3 or median intensity background on the area A2)). The positions and orientations of the areas A1, A2 and A3 is illustrated in FIG. 13. Calculate the estimated substance intensity as median of the detection area. Calculate the start value for the iteration step as average of the estimated background intensity and the estimated substance intensity.

In step $\chi 11$, the global threshold value is iterative adjusted, between a maximum intensity value, defined by the estimated substance intensity, and a min value, defined by the estimated background intensity, so that the average number of pixels in the y-direction (the angular direction) inside the approximate position of the detection area is equal to the detection area width.

In step $\chi 12$, the calculated global threshold value is used for binary encoding a stored image, in particular the stored disturbance filtered image into a binary coded disturbance filtered image.

D. Step δ: Remove Binary Objects Outside the Detection Area

The object of the following steps δ–δ2, is to remove any disturbances outside the detection area. The following algorithm processes the data of the binary coded disturbance filtered image, in which all objects are set to 1, i.e., binary high. Further, it is assumed that there is no object to be removed inside the boarders of the approximately calculated detection area position, and the detection area is the largest area of the image.

Figure 10:
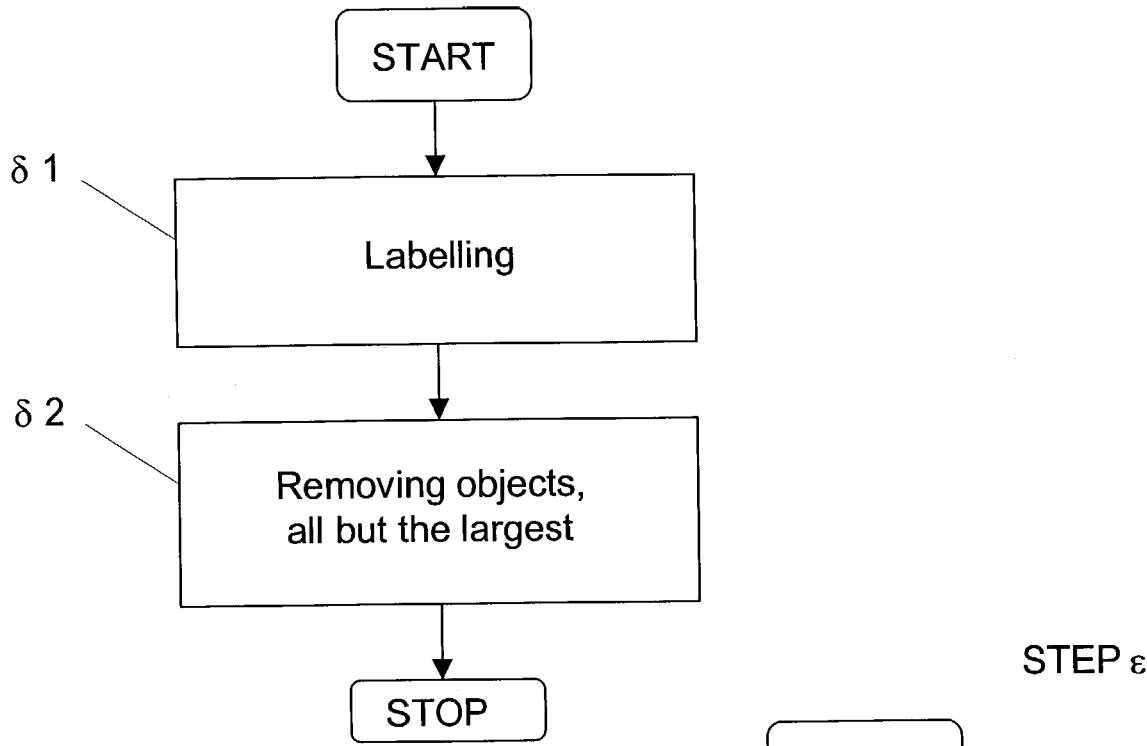
FIG. 10 is a flowchart illustrating a method step $\delta$ according to the invention.

In FIG. 10, step δ for removing binary objects outside the detection area is presented schematically in a flowchart.

The first step, step δ1: labelling of all the objects in the binary coded disturbance filtered image, wherein the number of connected pixels, i.e., the area, of each object is determined. Labelling is a known method in image processing.

The second step, step δ2: generating a binary detection area image by removing all but the largest objects that are inside the approximate detection area position.

E. Step ε: Removing Unwanted Areas of the Detection Area

Sometimes the object is to calculate an amount for a "normalized" area, i.e., a predefined amount of pixels, inside the detection area. This is done to minimize the variance between detection areas on the same microfluidic device. The variance depends among other things on background radiation, such as fluorescence, from the detection area. It is assumed that the 3D distribution of an intensity signal inside the detection area is independent of small variations in the detection area length. The substance signal deriving from a portion of the detection area that may be closest to the inlet of the corresponding detection microcavity. The algorithm used is a process for generating a new binary image that only comprises pixels within the normalized area ((detection area width) multiplied by (min detection area length)) in the binary detection area image starting from the inner part of the CD.

Figure 11:
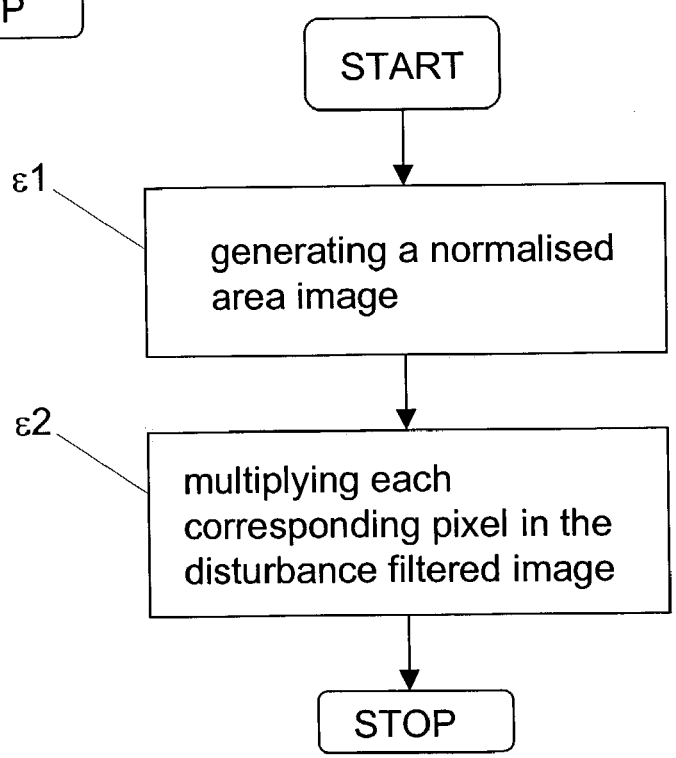
FIG. 11 is a flowchart illustrating a method step $\epsilon$ according to the invention.

In FIG. 11, step ε for removing unwanted areas of the detection area is presented schematically in a flowchart.

The first step, step ε1: generating a normalized area image by setting all binary high indicated pixels outside the location of the normalized area ((detection area width) multiplied by (min detection area length)) to binary "low" in the binary detection area image.

The second step, step ε2: multiplying each corresponding pixel in the disturbance filtered image, generated and stored earlier in the invented process, and the normalized area image with each other and perform a calculation, e.g., integration, on the normalized area.

F. Step φ: Apply Default Detection Area in Noisy Images

The described method above will not work properly, or not at all, for very noisy images hiding the substance signal. The following algorithm works, if all processed images originate from the same set of detection areas, e.g., the same CD. The detection areas are then well-defined in angular position and quite well in radius direction.

During the algorithm to locate the position of the detection area within the search area, all positions for detection areas having high confidence are stored.

Figure 12:
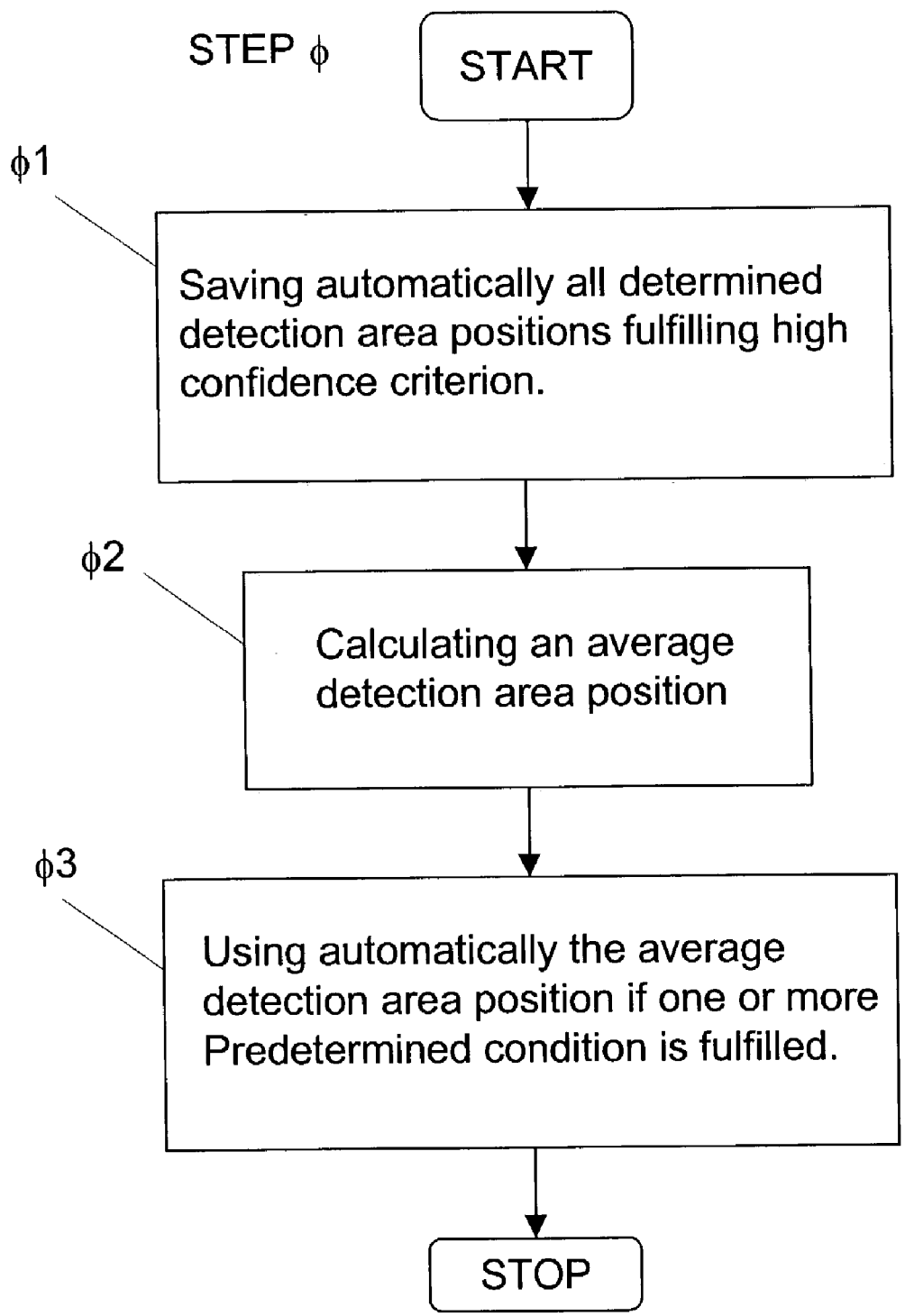
FIG. 12 is a flowchart illustrating a method step $\phi$ according to the invention.

In FIG. 12, step φ for applying a default detection area in noisy images is presented schematically in a flowchart.

The method for applying default detection area in noisy images may comprise following steps:

Step φ1: Saving automatically all determined detection area positions (step χ) fulfilling high confidence criterion.

Step φ2: Calculating an average detection area position.

Step φ3: Using automatically the average detection area position if one or more predetermined condition is fulfilled.

The average position for a detection area will automatically be applied for all calculated detection areas that fulfil all following conditions:

It's angular start position differ from the average start position more than [amount] multiplied by [detection area width], wherein the [amount] is chosen 0–1.

The average number of binary high pixels, in the normalized area image, in angular direction for all radiuses is less than [amount] multiplied by [detection area width], wherein the [amount] is chosen 0–1.

The difference between angular stop and start positions is greater than [amount] multiplied by [detection area width], wherein the [amount] is chosen 1–10.

The number of binary high pixels, in the normalized area image, in angular direction for all radiuses is less than

[amount] multiplied by [detection area width] multiplied by [min detection area length], wherein the [amount] is chosen 0–1.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method for reducing noise in a substance raw data image having substance and noise data which is associated to one detection microcavity and one substance present in the detection microcavity of a microchannel structure of a microfluidic device, said method comprises the steps of:
   obtaining substance raw data information using a detector arrangement capable of scanning and collecting radiation data in a search area associated to a detection area of the microfluidic device:
   storing collected radiation data as measure data for the amount of the substance as substance raw data in a set in a data storage, and:
   reducing background radiation data either by use of a image comprising background radiation data and no substance data information, a background radiation image, or by use of a calculated median value of the background radiation data.

2. The method of claim 1, wherein the method further comprises the steps of:
   accessing a background radiation image or generating a background radiation image;
   accessing corresponding substance raw data image or generating a substance raw data image;
   correlating the two images and generating a correlation image;
   locating the positions of the largest pixel values; and
   positioning the images correctly, subtracting corresponding pixel values and storing the generated background processed image.

3. A computer program product directly stored into an internal memory storage of a processing unit within the computer means comprises the software code means for performing the step of claim 1.

4. A computer program product stored on a computer usable medium, comprising readable program for causing a processing unit in a computer means to control an execution of the method of claim 1.

5. The computer program product of claim 4, wherein the computer usable medium is a record medium.

6. The computer program product of claim 4, wherein the computer usable medium is a computer memory.

7. The computer program product of claim 4, wherein the computer usable medium is a read-only Memory.

8. An arrangement for reducing noise in a substance raw data image of having substance and noise data which is associated to one detection microcavity and one substance retained in the detection microcavity of a microfluidic structure of a microfluidic device,
   means for obtaining substance raw data information by scanning and collecting radiation data in a search area associated to a detection area of said microfluidic device, which is associated to the detection microcavity;
   means for storing the collected radiation data as measure data for the amount of the substance as substance raw data in a set in a data storage;
   means, for controlling the arrangement; and
   means for reducing background radiation data either by use of an image comprising background radiation data and no substance data information or by use of a calculated median value of the background radiation data.

9. The arrangement of claim 8, wherein the arrangement further comprises:
   means for accessing a background radiation image and means for generating a background radiation image;
   means for accessing corresponding substance raw data image and means for generating a substance raw data image;
   means for correlating the two images and generating a correlation image;
   means for locating the positions of the largest pixel values; and
   means for positioning the images correctly, means for subtracting corresponding pixel values and means for storing the generated background processed image.

* * * * *